United States Patent [19]
Doi et al.

[11] Patent Number: 5,354,664
[45] Date of Patent: Oct. 11, 1994

[54] DNA ENCODING A HUMAN THROMBOMODULIN HAVING A MODIFIED GLYCOSAMINOGLYCAN (GAG) BINDING SITE

[75] Inventors: Takeshi Doi, Tsukuba; Akio Iwasaki, Matsudo; Yushi Saino, Tokyo; Shigeru Kimura, Higashiyama; Masao Ohkuchi, Tokorozawa, all of Japan

[73] Assignee: Kowa Co., Ltd., Nagoya, Japan

[21] Appl. No.: 110,011

[22] Filed: Aug. 23, 1993

Related U.S. Application Data

[60] Division of Ser. No. 14,723, Feb. 8, 1993, Pat. No. 5,273,962, which is a continuation-in-part of Ser. No. 796,336, Nov. 22, 1991, abandoned.

[30] Foreign Application Priority Data

Nov. 30, 1990 [JP] Japan .................................. 2-335720
Feb. 25, 1991 [JP] Japan .................................. 3-30271

[51] Int. Cl.$^5$ ........................ C12N 15/15; C12N 5/10
[52] U.S. Cl. .................................. 435/69.1; 530/381; 536/23.1; 536/23.5; 435/320.1; 435/240.2

[58] Field of Search ..................... 536/23.1, 23.5; 435/69.1, 240.2, 320.1; 530/381

[56] References Cited

PUBLICATIONS

Jackman, R. W., et al. (1987) *Proc. Natl. Acad. Sci. USA* 84: 6425-6429.
Parkinson, J. F., et al. (1990) *Biochem. Biophys. Res. Comm.* 169(1): 177-83.
Nawa, K., et al. (1990) *id.* 171(2): 729-37.
Bourdon, M. A., et al. (1986) *J. Biol. Chem.* 261(27): 12534-37.

*Primary Examiner*—Robert J. Hill, Jr.
*Assistant Examiner*—David L. Fitzgerald
*Attorney, Agent, or Firm*—Oblon, Spivak, McClelland, Maier & Neustadt

[57] ABSTRACT

Thrombin-binding substances capable of promoting anti-thrombin III activity and inhibiting platelet aggregation, and by themselves possessing anti-thrombin activity are disclosed. The thrombin-binding substances are useful as an effective component of anticoagulant agents, and can be produced inexpensively on a large scale.

9 Claims, 2 Drawing Sheets

DNA ENCODING A HUMAN THROMBOMODULIN HAVING A MODIFIED GLYCOSAMINOGLYCAN (GAG) BINDING SITE

CROSS REFERENCE TO RELATED APPLICATION

This is a division of application Ser. No. 08/014,723, filed on Feb. 8, 1993, now U.S. Pat. No. 5,273,962, which is a continuation-in-part of 07/796,336 filed Nov. 22, 1991, now abandoned.

BACKGROUND OF THE INVENTION

1. Field of the Invention

The present invention relates to a novel thrombin-binding substance, a DNA fragment encoding the amino acid sequence of said thrombin-binding substance, a recombinant vector comprising said DNA fragment, a transformed cell harboring said recombinant vector, an anticoagulant composition comprising said thrombin-binding substance which has platelet aggregation inhibitory activity, and a process for the preparation of said thrombin-binding substance.

2. Description of the Background Art

A great deal of work has been done regarding the role that thrombin plays as a proteolytic enzyme in the blood coagulation control mechanism, and the mechanism of blood coagulation has been elucidated for the most part.

A publication reports that thrombin activates Protein C which is said to act on the fibrinolytic and anticoagulant systems and that there is a certain substance in extracts of rabbit lung tissues which functions as a coenzyme for the activation mechanism. Such a substance was named thrombomodulin [N. L. Esmon et at, *J. Biological Chemistry*, 257, (2), 859-864 (1982)].

N. Aoki, et al reported that a human thrombomodulin separated from human placenta with a molecular weight of about 71,000 under nonreducing conditions had characteristics similar to the thrombomodulin reported by Esmon et al [Thromb. Res., 37, 353-364 (1985)].

I. Maruyama et al compared the activities of human thrombomodulin separated from human placenta having a molecular weight of about 75,000 with the activities of the above-mentioned rabbit thrombomodulin. They reported that the two thrombomodulins were equivalent in activity [*J. Clin. Invest.*, 75, 987-991 (1985)].

H. Ishii et al reported that human plasma and human urine contained substances having the same activities as thrombomodulin and that the molecular weights of such substances in plasma were 63,000 and 54,000 [*J. Clin. Invest.*, 76, 2178-2181 (1985)].

The present inventors previously discovered two types of thrombin-binding substances in human urine. They are different from the above-mentioned substances; having smaller molecular weights, i.e., about 39,000 and 31,000 under nonreducing conditions. The present inventors filed a patent application on these substances (Japanese Patent Laid-open (kokai) No. 146898/1988).

Furthermore, the present inventors separated two types of thrombin-binding substances (A) and (B) from human urine and a culture broth of cells derived from human tissues, and established a process for producing large amounts of these thrombin-binding substances in a stable manner. The present inventors previously filed patent applications on the thrombin-binding substances and the process (European Patent Publication No. 455,681).

The present inventors obtained a human urine derived thrombin-binding substance using a recombinant DNA technique (r-UTM) and filed a patent application on this process (Japanese Patent Application No. 54446/1990).

The thrombin binding substance of the present invention is distinguished over the known (r-UTM) binding substance by the addition of the amino acid sequence $X_1X_2Y_1SerGlySerGlyY_2$ (SEQ ID NO: 17) at the carboxyl end of the r-UTM protein.

Thrombomodulin from rabbit lungs is known to increase the activity of antithrombin III [K. T. Preissner et al, *J. Biological Chemistry*, 265, 4915-4922 (1990)]. Such an activity, however, is not possessed by thrombomodulin from bovine [H. V. Jakubowski et al, *J. Biological Chemistry*, 261, 3876 (1986)], and thrombomodulin from human placenta inhibits the activity of antithrombin III [K. Hirahara et al, *Thrombo. Res.*, 57, 117-126 (1990)].

Also, two soluble thrombomodulins produced by genetic manipulation techniques are known in the art. One is known to increase the activity of antithrombin III and another is known to possess no such capability [K. Nawa et al, *Biochem. Biophys. Res.*, 171, 729-737 (1990)]. These thrombomodulins, however, are known to inhibit the thrombin coagulation in platelet which plays an important role in the blood coagulation system, but not to inhibit an ADP coagulation effect [N. L. Esmon, *J. Biological Chemistry*, 256, 12238-12242 (1983)].

Promoting the antithrombin III activity and the platelet aggregation inhibitory activity in human thrombomodulins and other thrombin-binding substances has therefore been desired.

SUMMARY OF THE INVENTION

In view of this situation, the present inventors have undertaken extensive studies and found that a transformant prepared by transforming a host cell with a recombinant vector into which a DNA fragment obtained by combining a specific DNA fragment at the 3'-end of a DNA fragment encoding a thrombin-binding substance derived from human urine is combined can produce a thrombin-binding substance derived from human urine capable of increasing an antithrombin III activity and inhibiting platelet aggregation.

Accordingly, an object of the present invention is to provide a novel thrombin-binding substance having the following amino acid sequence (hereinafter referred to as "Sequence A") [SEQ ID NO: 18], a DNA fragment having the nucleotide sequence encoding Sequence A, a recombinant vector comprising said DNA fragment and a replicable vector, and a transformed cell harboring said recombinant vector.

<Sequence A>
AlaProAlaGluProGlnProGlyGlySerGlnCysValGluHisAspCysPheAlaLeu
TyrProGlyProAlaThrPheLeuAsnAlaSerGlnIleCysAspGlyLeuArgGlyHis
LeuMetThrValArgSerSerValAlaAlaAspValIleSerLeuLeuLeuAsnGlyAsp -continued GlyGlyValGlyArgArgArgLeuTrpIleGlyLeuGlnLeuProProGlyCysGlyAsp
ProLysArgLeuGlyProLeuArgGlyPheGlnTrpValThrGlyAspAsnAsnThrSer
TyrSerArgTrpAlaArgLeuAspLeuAsnGlyAlaProLeuCysGlyProLeuCysVal
AlaValSerAlaAlaGluAlaThrValProSerGluProIleTrpGluGluGlnGlnCys
GluValLysAlaAspGlyPheLeuCysGluPheHisPheProAlaThrCysArgProLeu
AlaValGluProGlyAlaAlaAlaAlaAlaValSerIleThrTyrGlyThrProPheAla
AlaArgGlyAlaAspPheGlnAlaLeuProValGlySerSerAlaAlaValAlaProLeu
GlyLeuGlnLeuMetCysThrAlaProProGlyAlaValGlnGlyHisTrpAlaArgGlu
AlaProGlyAlaTrpAspCysSerValGluAsnGlyGlyCysGluHisAlaCysAsnAla
IleProGlyAlaProArgCysGlnCysProAlaGlyAlaAlaLeuGlnAlaAspGlyArg
SerCysThrAlaSerAlaThrGlnSerCysAsnAspLeuCysGluHisPheCysValPro
AsnProAspGlnProGlySerTyrSerCysMetCysGluThrGlyTyrArgLeuAlaAla
AspGlnHisArgCysGluAspValAspAspCysIleLeuGluProSerProCysProGln
ArgCysValAsnThrGlnGlyGlyPheGluCysHisCysTyrProAsnTyrAspLeuVal
AspGlyGluCysValGluProValAspProCysPheArgAlaAsnCysGluTyrGlnCys
GlnProLeuAsnGlnThrSerTyrLeuCysValCysAlaGluGlyPheAlaProIlePro
HisGluProHisArgCysGlnMetPheCysAsnGlnThrAlaCysProAlaAspCysAsp
ProAsnThrGlnAlaSerCysGluCysProGluGlyTyrIleLeuAspAspGlyPheIle
CysThrAspIleAspGluCysGluAsnGlyGlyPheCysSerGlyValCysHisAsnLeu
ProGlyThrPheGluCysIleCysGlyProAspSerAlaLeuValArgHisIleGlyThr
AspCysAspSerGlyLysValAspX1 X2 Y1 SerGlySerGlyY2, (SEQ ID NO: 18)

wherein X1 and X2 represent acidic amino acids and Y1 and Y2 represent any arbitrary amino acids.

Another object of the present invention is to provide an anticoagulant composition comprising said thrombin-binding substance and exhibiting platelet aggregation inhibitory activity.

Still another object of the present invention is to provide a process for the preparation of said thrombin-binding substance.

Other objects, features and advantages of the invention will hereinafter become more readily apparent from the following description.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION AND PREFERRED EMBODIMENTS

Figure 1:
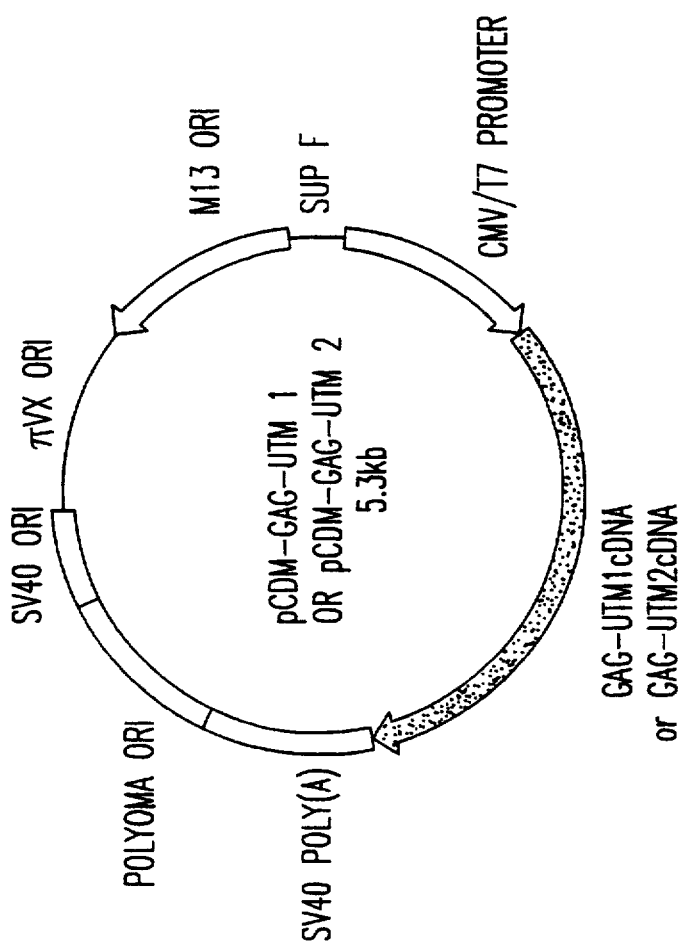
FIG. 1 is a scheme illustrating the structure of expression vector, pCDM-GAG-UTM1 and pCDM-GAG-UTM2, of the present invention.

The thrombin-binding substance of the present invention can be prepared, for example, according to the following process. A template DNA is first prepared by cutting a human placenta genome DNA with a suitable restriction endonuclease. The template DNA is screened using, as a probe, a DNA primer synthesized referring to a nucleotide sequence of a known human thrombomodulin gene [Shirai, T et al, *J. Biochem*, 103, 281–285 (1988)]. The DNA thus produced is fragmented with a suitable restriction endonuclease, and DNA fragments thus obtained are ligated with a cloning vector to transform the microorganism. A plasmid DNA is extracted from the transformant and treated with a restriction endonuclease to produce a DNA fragment containing 1404 bases encoding the thrombin-binding substance derived from human urine. An oligonucteotide having a nucleotide sequence encoding an amino acid sequence, $X_1X_2Y_1$SerGlySerGly$Y_2$, (SEQ ID NO: 1) is inserted into the DNA fragment, thus obtaining a DNA fragment which contains the DNA fragment of the present invention. Typical examples of DNA fragments of the present invention are those having a nucleotide sequence of SEQ ID No. 3 and SEQ ID No. 4. The DNA fragments of the present invention, however, are not limited to them. Any DNA fragments capable of encoding an amino acid sequence constituting the thrombin-binding substance which is the target of the present invention, i.e., the Sequence A, preferably SEQ ID No. 1 and SEQ ID No. 2, are included in the present invention.

The construction of the recombinant vector containing the DNA fragment of the present invention may be carried out by connecting the DNA fragment of the present invention with a replicable expression vector.

As the expression vector, those from any sources, e.g., procaryotes (typically *E. coli*), yeasts, insect viruses, vertebrate viruses, etc., can be used, so long as they are replicable.

In order to ensure efficient production of the thrombin-binding substance, it is desirable that the recombinant expression vector be constructed from the following nucleotide sequences (1) to (7) in this order toward the downstream direction of the transcription.

(1) A nucleotide sequence acting as a promoter.

(2) A nucleotide sequence functioning as a ribosome binding site.

(3) A nucleotide sequence acting as a initiation codon.

(4) A nucleotide sequence encoding a signal peptide.

(5) A nucleotide sequence encoding the amino acid sequence of Sequence (A).

(6) A nucleotide sequence acting as a termination codon.

(7) A nucleotide sequence acting as a poly A addition signal.

A plasmid DNA is preferably used as a vector, for instance, a plasmid which can multiply itself, e.g., in *E. coli* as a host microorganism, and can express the inserted gene by transforming mammalian cells. Such a plasmid DNA comprises nucleotide sequences required for the plasmid to multiply itself in *E. coli*, such as a nucleotide sequence acting as a replicator of ColEI plasmid series, a nucleotide sequence acting as a promoter in mammalian cells, a gene functioning as a selection marker of the transformed *E. coli*, and a gene functioning as a selection marker of the transformed mammalian cells. In a preferable embodiment, it further include a replicator nucleotide sequence such as SV40 ori, polyoma ori, or HSV ori which functions in mammalian cells. Given as preferable examples of promoters are promoters, e.g., cytomegalovirus, SV40, polyoma virus, bovine papilloma virus, adenovirus, etc; retrovirus LTR, e.g., MMTV; a promoter of metallothionein gene, and the like. Examples of E. coli selection markers are ampicillin resistant genes, kanamycin resistant genes, tetracycline resistant genes, chloramphenicol resistant genes, and the like. Given as examples of mammalian cell selection markers are neomycin resistant genes, hygromycin B resistant genes, thymidine kinase genes, dihydrofolate reductase genes, xanthine-guanine phosphoribosyl transferase genes, and the like. These genes can be used either singly or in combination of two or more.

Incorporation of the DNA fragment of the present invention into the above vectors can be carried out by cutting a DNA containing the DNA fragment with a suitable restriction endonuclease, optionally, adding a suitable linker, and combining it with the vector which is cut by a suitable restriction endonuclease. Restriction endonucleases which can be used here are, for example, Eco RI, Sph I, Pst I, Hind III, Bam HI, Xho I, Xba I, Ban III, Sma I, Nco I, and the like. Nucleotide modification enzymes such as exonuclease III, Ba131, SI nuclease, exonuclease VII, mungbean nuclease, DNA polymerase, and the like can also be used. As a linker, Eco RI linker, Sma I linker, Nco I linker, Bam HI linker, Xho I linker, Hind III linker, Pst I linker, Sph I linker, XbaI I linker, or the like may be used.

Transformed cells which can efficiently produce the recombinant vector and/or thrombin-binding substance of the present invention can be obtained by introducing the expression recombinant vector obtained by the above method into host cells by means of the competent cell method, the protoplast method, the calcium phosphate coprecipitation method, the electroporation method, the DEAE dextran method, the lipofectin method, or the like. Unicellular organisms, such as bacteria and yeasts, cultured insect cells, cultured vertebrate cells, and the like are preferably used as host cells for obtaining the transformant. Various mutants of E. coli K12 strain, e.g., HB101, C600K, JM101, JM103, JM105, JM109, MV1034, MV1184, MC1061/P3, and the like, are preferably used as E. coli host cells. Preferable examples given of mammalian cells are COS cells, CHO cells, L cells, C127 cells, NIH3T3 cells, HeLa cells, and the like.

The thrombin-binding substance can be obtained by cultivating the transformant thus obtained, extracting and separating it from the cultivated cells or the culture broth. Various natural or artificial media can be used for the cultivation of the transformed cells. The media preferably contain carbon sources such as sugars, alcohols, and salts of organic acids; nitrogen sources such as protein mixtures, amino acids, and ammonium salts; and inorganic salts. In addition, vitamins and antibiotics corresponding to the selection marker genes may preferably be included. If the vector is of the type of which the expression can be controlled, it is necessary to add a procedure for inducing the expression in the course of the cultivation. After the cultivation, the culture broth is centrifuged to separate culture liquid from the cells. In the case where the thrombin-binding substance accumulates in the cultured cells, the cells are destroyed by means of freeze-thaw, ultrasonic treatment, French press, enzyme treatment, homogenizing, or the like, and the thrombin-binding substance is dissolved by using EDTA, surfactants, urea, guanidine hydrochloride, or the like.

A purified thrombin-binding substance can be obtained by submitting the culture liquid or the cell extract containing the thrombin-binding substance thus prepared to column chromatography. Ion-exchange chromatography, affinity chromatography, e.g., that using the monoclonal antibody described in Japanese Patent Laid-open (kokai) No. 45398/1989, gel filtration chromatography, or the like can be used either independently or in combination. Among the thrombin-binding substances thus obtained those having the amino acid sequence of SEQ ID No. 1 or SEQ ID No. 2 possess the following characteristic.

(1) Amino acid sequence:
Based on the nucleotide sequence of the DNA fragments, the amino acid sequence is considered to be those shown in SEQ ID Nos. 1 and 2.

(2) Molecular weight:
55,000–100,000 determined by the SDS-polyacrylamide gel electrophoresis under under nonreduced conditions.

(3) Isoelectric point:
pH 3–4 determined by the isoelectric electrophoresis method using ampholite.

(4) Sugar analysis:
Two or more sugars are considered to be attached to the thrombin-binding substances from the molecular weight. Based on the amino acid sequence, one of the sugars is considered to be an acidic polysaccharide attached to Ser (474).

(5) Actions:
Possesses antithrombin activity.
Increases the activity of the antithrombin III.
Possesses platelet aggregation inhibitory activity.

Injection preparations are typical examples of the composition comprising the thrombin-binding substance of the present invention as an anticoagulant agent. A preferable form of such injection preparations is a freeze-dried powder which can be dissolved into distilled water or physiological saline each time it is administered. Intravenous injection is a preferable manner by which the preparation is administered.

Although a dose depends on the symptoms of the patient, the body weight, and the like, a preferable dose is 10 µg/kg to 10 mg/kg. The thrombin-binding substance of the present invention induces no abnormality with the dose of the above range. It is a quite safe substance.

Other features of the invention will become apparent in the course of the following description of the exemplary embodiments which are given for illustration of the invention and are not intended to be limiting thereof.

EXAMPLES

Example 1

Cloning of thrombin-binding substance gene

Primer #1 having the sequence of SEQ ID No. 5 and primer #2 having the sequence of SEQ ID No. 6 were synthesized by using a DNA synthesizer (ABI Model 381A) referring to the nucleotide sequence of human thrombomodulin gene [Shirai, T et al, J. Biochem, 103, 281–285 (1988)]. A template DNA was prepared by digesting a human placenta genome DNA (a product of Clonetech Co.) with Bam HI. The gene amplification was carried out in the reaction solution of the following formulation using Quick Thermo System (Model QTS-10M: trademark, manufactured by Japan Genetic Co.) by the repetition of 30 cycles of incubation; one cycle consisted of incubation at 94° C. for 2 minutes, at 50° C. for 3 minutes, and at 72° C. for 4 minutes. After the reaction, a portion of the reaction product was sampled to confirm amplification of the target DNA band by agarose gel electrophoresis.

| <Reaction Solution> | |
|---|---|
| Distilled water | 71 μl |
| Buffer solution* | 10 μl |
| dNTP mixed solution (2.5 mM) | 8 μl |
| Primer #1 (20 μM) | 5 μl |
| Primer #2 (20 μM) | 5 μl |
| Template DNA (1 μg/μl) | 1 μl |
| AmpliTaq (5 units/μl) | 0.5 μl |

*Buffer solution:
0.1M potassium chloride
0.1M Tris-HCl buffer (pH 8.3)
0.1% gelatin
15 mM magnesium chloride DNA was collected from the reaction solution by ethanol precipitation, digested with Xho I and Kpn I and subjected to the agarose gel electrophoresis to obtain 1.57 kb Xho I-Kpn I fragments. Separately, the vector for the cloning pUC118 [Vieira, J. and Messing, J., Methods Enzymol., 153, 3–11 (1987)] was digested with Hind II, connected with Xho I linker, and further digested with Xho I and Kpn I to obtain vector fragments by the agarose gel electrophoresis. The vector fragments and the 1.57 kb Xho I-Kpn I fragments were ligated and E. coli MV1034 [Vieira, J. and Messing, J., Methods Enzymol., 153, 3–11 (1987)] was transformed with the ligated DNA.

Plasmid DNA was extracted from the transformant thus obtained and digested with restriction endonuclease. In this manner, 6 clones holding a plasmid to which the 1.57 kb Xho i-Kpn I fragment derived from human thrombomodulin gene was inserted were selected.

The determination of nucleotide sequences of the inserted fragments in clones thus obtained revealed 1 to 3 mutated sites in each fragment. Then, 0.31 kb Xho I-Sma I fragment from clone 2, 0.65 kb Sma I-Mlu I fragment from clone 1, and 0.62 kb Mlu I-Kpn I fragment from clone 4, all without mutated sites, were recombined with the above-mentioned vector fragment to obtain plasmid pUCTM/XHO-KPN containing an inserted fragment of the human thrombomodulin gene with the correct sequence.

Example 2

Construction of the vector for the expression of thrombin-binding substance

In order to combine a glycosaminoglycan addition site to Asp at C-terminal of the amino acid sequence of the thrombin-binding substance derived from human urine, linkers $1 to $6 with the nucleotide sequences of SEQ ID Nos. 7 to 12, respectively, were synthesized and each 5'-end was phosphorylated.

The pUCTM/XHO-KPN was digested with Xho I and Kpn I to prepare a 1.57 kb Xho I-Kpn I fragment derived from a human thrombomodulin gene. This 1.57 kb fragment was ligated with a mammalian cell expression vector CDM8 (a product of Invitrogen Co.) which had been digested with Xho I and dephosphorylated together with linkers $1, $2, $3, and $4. The 1.57 kb fragment was also ligated with Xho I digested and dephosphorylated CDM8 with linkers $1, $2, $5, and $6.

E. coli MC1061/P3 [Seed, B. and Aruffo, A., Proc. Natl. Acad. Sci., USA, 84, 3365–3369 (1987)] was transformed with the ligated DNAs. Plasmid DNAs were extracted from the transformants thus prepared and digested with restriction endonucleases to confirm the direction and the site of the insertion. 1.68 kb fragments containing the DNA fragment of the present invention were cut out by Xho I from 8 clones which showed the correct direction of insertion and the correct restriction endonuclease map. The nucleotide sequences of all clones were found to have the sequence of SEQ ID No. 13 or 14, confirming that the expression vectors were correctly constructed.

The expression vector of the present invention thus obtained were named pCDM-GAG-UTM1 and pCDM-GAG-UTM2 (FIG. 1), and the transformant harboring the vectors were named E. coli MC1061/P3 (pCDM-GAG-UTM1) and E. coli MC1061/P3 (pCDM-GAG-UTM2).

Example 3

Expression of the thrombin-binding substance by cultured mammalian cells

COS7 cells were transfected with pCDM-GAG-UTM1 or pCDM-GAG-UTM2 by the DEAE-Dextran method [Seed, B. and Aruffo, A., Proc. Natl. Acad. Sci., USA, 84, 3365–3369 (1987)]. $5 \times 10^5$ cells were inoculated into a 60 mm culture dish and, on the next day, the culture medium was aspirated and replaced by 2 ml of Dulbecco's-modified minimum essential medium (DMEM) containing 10% Nu-serum (Collaborative Research). 10 μg (1 μg/μl) of pCDM-GAG-UTM1 or pCDM-GAG-UTM2 were added to 100 μl of a 10 mg/ml DEAE-Dextran solution (average molecular weight: $5 \times 10^5$, a product of Pharmacia) in PBS, and the resulting solution was added to cell culture liquid together with 10 μl of 20 mM chloroquine. After cultivating for 4 hours at 37° C., the culture medium was aspirated and 2 ml of 10% DMSO (dissolved in PBS) was added. The mixture was allowed to stand at room temperature for 2 minutes. After removal of the DMSO solution by aspiration, 3 ml of DMEM containing 10% FCS was added and the mixture was cultivated at 37° C. for 24 hours. The culture medium was replaced by DMEM containing no FCS, followed by continued cultivation for a further 48 hours. After the cultivation, the supernatant was collected.

The culture medium obtained by the above procedure was passed through a 1 ml Sepharose 4B (2 mg IgG/ml resin) column with which monoclonal antibody A-73 (Japanese Patent Laid-open (kokai) No. 45398/1989; 2 mg IgG/ml resin) was combined. The column was washed with (1) 2 ml of 0.02M Tris-HCl buffer (pH 7.4) containing 0.1M NaCl, (2) 20 ml of 0.02M Tris-HCl buffer (pH 7.4) containing 1M NaCl and 0.05% Tween 20, and (3) 5 ml of 0.02M Tris-HCl buffer (pH 7.4) containing 1M NaCl, followed by elution with 5 ml of 0.02M Tris-HCl buffer (pH 7.4) containing 2M sodium thiocyanate, 5 mM EDTA, and 1M NaCl. The eluate was dialyzed against 50 mM acetate buffer containing 0.1M NaCl (pH 4.5) and applied on a column of Mono-Q sepharose. The column was washed with the same buffer and eluted with linear gradient of 0.1 to 2 M NaCl in 50 mM acetate buffer (pH 4.5) to obtain purified thrombin-binding substances (r-GAG-UTM1 and r-GAG-UTM2).

Example 4-a

Expression of the thrombin-binding substance by cultured mammalian cells

CHO.K1 cells were transfected with pCDM-GAG-UTM1 by the calcium phosphate method [Gorman, C., "DNA Cloning" IRL Press, England, vol. 2, 143-190 (1985)]. $5 \times 10^5$ CHO.K1 cells were inoculated into a 10 cm petri dish and, on the next day, the culture medium (Ham F12 medium containing 10% FCS, hereinafter referred to as Medium) was exchanged. Four (4) hours thereafter, a coprecipitate of DNA and calcium phosphate was added. The coprecipitate used here was prepared according to the following manner. 20 µg of pCDM-GAG-UTM1 and 100 ng of neomycin resistant gene dissolved into 450 µl of 1 mM Tris-HCl buffer <pH 8.0)−0.1 EDTA and mixed with 50 µl of 2.5M calcium chloride. The mixture was added dropwise to 500 µl of solution: 50 mM HEPES (pH 7.12)−280 mM NaCl−1.5 mM sodium hydrogen phosphate, and after allowing to stand still, the solution was added to the cell culture medium for cultivation for 24 hours. The medium was replaced by a fresh one and cultivated for a further 24 hours, following which the medium was replaced by a selective medium containing 400 µg/ml G418. After 2 weeks, colonies produced were transferred to a 24-well plate and continuously cultivated until confluent. The supernatant was collected from the culture broth. The secreted thrombin-binding substance (r-GAG-UTM1) was quantitatively analyzed to select high producing clones. The cloning was further carried out on the selected clone by the limiting dilution method. The transformed cells thus obtained was named CHO-GUTM 1-8 and deposited with Fermentation Research Institute, Agency of Industrial Science and Technology (FERM P-3260).

The transformed cell CHO-GUTM 1-8 was cultured in UC202 medium (a product of Nissui Pharmaceutical Co.) containing 1% FCS in a 225 cm² flask to become confluent, following which the medium was replaced by 50 ml of UC202 medium without containing FCS. After 1 week, the culture supernatant was collected and the same amount of the fresh medium not containing FCS was added. After cultivation for a further 1 week, the culture supernatant was collected and confirmed to contain 3-4 µg/ml thrombin-binding substance therein secreted.

The purified thrombin-binding substance was obtained according to the same procedure of the later part of Example 3.

Example 4-b

Figure 2:
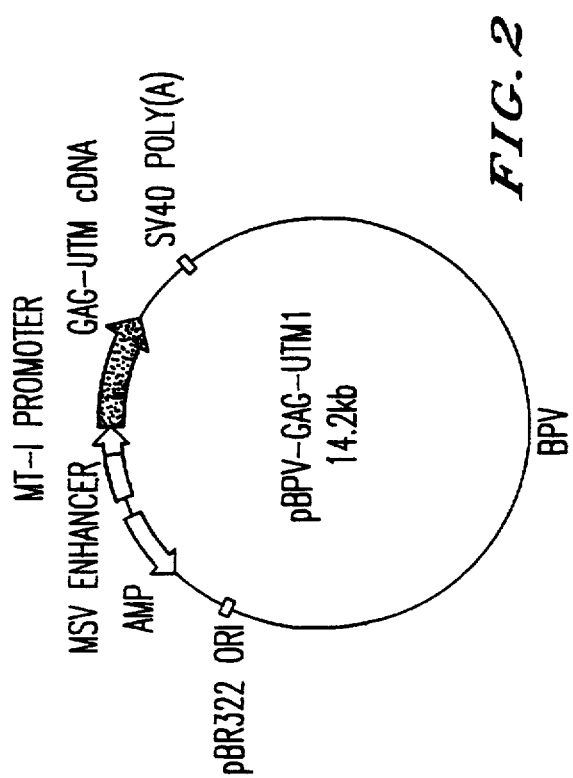
FIG. 2 is a scheme which illustrates the structure of expression vector pBPV-GAG-UTM1 of the present invention.

Construction of vector for the expression of thrombin-binding substance and expression of the substance by cultured mammalian cells pCDM-GAG-UTM1 was digested with Xho I to prepare a 1.7 kb fragment of soluble human modified thrombomodulin cDNA containing a site where glycosaminoglycan is bound to. Separately, a mammalian cell expression vector pBPV (a product of Pharmacia Co.) was digested with Xho I and dephosphorylated, and ligated with the cDNA fragment by the use of T4 DNA ligase for transforming E. Coli HB101 (product of TAKARA SHUZO K.K.). DNAs were extracted from the transformants thus prepared and digested with endonucleases to confirm the direction and the site of the insertion. Clones indicating the right direction and the site were selected. The expression vector of the present invention thus constructed was named pBPV-GAG-UTM1 (FIG. 2), and the transformant harboring the vector was named E. coli HB 101 (pBPV-GAG-UTM1).

In a similar manner as described in Example 4, mouse C127 cells were transfected with pBPV-GAG-U1 by the calcium phosphate method. $8 \times 10^5$ C127 cells were inoculated into a 10 petri dish and, on the next day, the culture medium (Dulbecco's Modified Eagle Minimal Medium (DMEM medium) containing 10% FCS) was exchanged. Four hours thereafter, a coprecipitate of DNA and calcium phosphate was added. The coprecipitate employed was prepared according to the following manner. Plasmid containing 20 µg of pBPV-GAG-UTM1 and 100 ng of neomycin resistant gene was dissolved into 450 µl of 1 mM Tris-HCl buffer (pH 8-0)−0.1 mM EDTA and mixed with 50µl of 2.5M calcium chloride. The mixture was added dropwise to 500 µl of a solution: 50 mMHEPES (pH 7.12)−280 mM NaCl−1.5 mM sodium hydrogen phosphate, and after allowing to stand over 30 minutes at room temperature, the solution was added to the cell culture medium for cultivation for 24 hours. The medium was replaced by a fresh DME medium and cultivated for a further 24 hours, and then the medium was replaced by a DME medium added with 5% FCS and containing 400 µg/ml G418. After 10 days, colonies produced were transferred to a 24-well plate and continuously cultivated up to the confluent. The supernatant was collected from the culture broth. The secreted thrombin-binding substance was quantitatively analyzed to select high producing clones. Cloning was further carried out on the selected clone by the limiting dilution method.

The selected transformed C127 cells were cultured in 5% FCS-added DMEM medium in a 1750 cm² roller bottle to become confluent, following which the medium was replaced by 500 ml of 1% FCS-added DMEM medium. After 1 week, the culture supernatant was collected and confirmed to contain 2 µg/ml thrombin-binding substance therein secreted.

About 800 µg of a purified thrombin-binding substance (r-GAG-UTM1) was obtained according to the procedure of the latter part of Example 3.

Example 5

Characteristics of thrombin-binding substance

SDS-PAGE was performed according to the Laemmli's method (Nature, 227, 680-685) on the purified thrombin-binding substances. The protein was transferred onto a PVDF membrane according to the Matsudaira's method [J. Biol. Chem., 262 (21), 10035-10038]. The PVDF membrane was then incubated in 0.05M Tris-HCl buffer (TBS) containing 0.1% bovine serum albumin and 0.1M NaCl at room temperature for 2 hours. After discharging the solution, the residue was washed thoroughly with a TBS-0.05% Tween 20, reacted with horseradish peroxidase conjugated monoclonal antibody A-60 in TBS-0.05% Tween 20 solution at room temperature for 1 hour. The solution was discharged, and the residue was washed thoroughly with a 0.05% Tween 20-TBS and put into 50 ml of an acetic acid buffer (pH 5.0) containing 5 mg of 3-amino-9-ethylcarbazole and 25 µl of 30% hydrogen peroxide to develop the color reaction to confirm a broad band which is characteristic to glycosaminoglycan adducts.

Example 6 r-UTM and r-GAG-UTM1 and 2 which are the thrombin-binding substances of the present invention, 0.1 μg/ml each, were treated with 5 μl of chondroitinase (10 mU, a product of Seikagaku Kogyo K.K.) at 37° C. for 40 minutes. The immunoblotting was carried out in the same manner as in Example 5 to confirm the presence of chondroitin sulfate type glycosaminoglycan covalent bonds in the thrombin-binding substances of the present invention.

Example 7

Anti-coagulant activity r-UTM and r-GAG-UTM1 and 2 of the thrombin-binding substance of the present invention, 2.5 μg/ml each, were mixed with human fibrinogen (2.5 mg/ml) and human antithrombin III (0 or 250 μg/ml), and dissolved in 5 mM solution of $CaCl_2$. Bovine thrombin (0.5 U/ml) was added to the solutions to measure the clotting time. The results are shown in Table 1.

TABLE 1

|  | Control (sec.) | r-UTM (sec.) | r-GAG-UTM1 (sec.) | r-GAG-UTM2 (sec.) |
|---|---|---|---|---|
| ATIII (−) | 43.3 | 61.8 | 77.2 | 80.1 |
| ATIII (+) | 49.5 | 80.8 | >400 | >400 |

Table I demonstrates that the thrombin-binding substances of the present invention delay blood coagulation by combining with thrombin. A remarkable promotion of the anti-coagulant activity of the thrombin-binding substances by the presence of antithrombin III are also shown.

Example 8

Anti-coagulant activity r-UTM (9-90 nM), r-GAG-UTM1, or r-GAG-UTM2 (thrombin-binding substance of the present invention (9-90 nM), dissolved in a solution of bovine fibrinogen (1 mg/ml) in 20 mM Tris-HCl buffer (pH 7.4) containing 0.15M NaCl, was mixed with bovine thrombin (18 nM) to measure the time required for the coagulation. 50% inhibitory concentrations ($IC_{50}$) were determined from the calibration curve prepared by using bovine thrombin of various concentrations. The results are shown in Table 2.

TABLE 2

|  | $IC_{50}$ (nM) |
|---|---|
| r-UTM | 80 |
| r-GAG-UTM1 | 16 |
| r-GAG-UTM2 | 15 |

Example 9

Anti-coagulant activity

Substances of the present invention (17 nM) or r-UTM (17 nM), dissolved in a solution of bovine fibrinogen (1 mg/ml) in 20 mM Tris-HCl buffer (pH 7.4) containing 0.15M NaCl, was mixed with bovine thrombin (18 nM) to measure the time required for the coagulation. The results are shown in Table 3.

TABLE 3

|  | Coagulation time (sec) |
|---|---|
| Control | 28.1 |
| r-UTM | 29.6 |
| r-GAG-UTM1 | 300.0 |
| r-GAG-UTM2 | 295.3 |

Example 10

Platelet aggregation inhibitory activity

To 8 μl of a solution of a substance of the present invention ($10^{-6}-10^{-8}$M) and platelet rich plasma (PRP) (200 μl), prepared from blood taken from rabbit ear vein, was added 2 μM adenosine diphosphate (ADP) to measure the platelet aggregation. 50% inhibitory concentration, i.e., the concentration of the compounds of the present invention to inhibit ADP aggregation, determined based on the calibration curve which was prepared by using ADP at various concentrations, were $2 \times 10^{-7}$M for r-GAG-UTM1 and $2.1 \times 10^{-7}$M for r-GAG-UTM2. r-UTM exhibited no aggregation inhibitory activity within the tested concentration range ($10^{-6}-10^{-8}$M).

Example 11

Changes in Blood Concentration

A catheter was inserted into the right femoral vein of Wistar rats (male) under anesthesia, and through the catheter were rapidly administered 1 mg/ml/kg of the tested compounds, r-GAG-UTM1 and r-UTM. Blood samples, 0.1 ml each, taken before the administration and 1, 3, 6, 10, 20, 30, 60, and 120 minutes after the administration were mixed with heparin and served as plasma samples for the determination of the blood concentration. The measurement of the blood concentration was performed according to the sandwich ELISA method using an anti-human thrombin-binding monoclonal antibody. Both tested compounds were found to be analyzable with the one-compartment model. The results are shown in the following Table.

TABLE 4

|  | r-GAG-UTM1 (n = 3) | r-UTM (n = 5) |
|---|---|---|
| $T_{1/2}$ (min) | 75.2 ± 10.8 | 45.4 ± 2.6 |
| AUC (min · μg/ml) | 1380 ± 61 | 872 ± 64 |

As illustrated above thrombin-binding substances of the present invention promote antithrombin III activity and inhibit platelet aggregation, and by themselves possess antithrombin activity. Thus, they are useful as an effective component of anticoagulant agents. Furthermore, the thrombin-binding substance of the present invention can be produced inexpensively in a large scale.

Obviously, numerous modifications and variations of the present invention are possible in light of the above teachings. It is therefore to be understood that within the scope of the appended claims, the invention may be practiced otherwise than as specifically described herein.

We claim:

1. A DNA molecule, the sequence of which encodes the amino acid sequence of SEQ ID NO: 18, wherein Xaa[469] and Xaa[470] are acidic amino acids and Xaa[471] and Xaa[472] are arbitrary amino acids.

2. The DNA molecule of claim 1, wherein the encoded polypeptide has Glu[469], Asp[470], Tyr[471], and Glu[472].

3. The DNA molecule of claim 1, wherein the encoded polypeptide has Asp[469], Glu[470], Ala[471], and Asp[472].

4. A DNA molecule having the nucleotide sequence of SEQ ID NO: 3.

5. A replicable recombinant vector comprising the DNA sequence of claim 1.

6. A vector comprising, in order (5'→3'):
   a promoter sequence;
   a ribosome binding sequence;
   an initiation codon;
   a sequence encoding a signal peptide;
   a sequence encoding a mature translation product according to claim 1;
   a termination codon; and
   a polyA addition signal.

7. A DNA molecule having the nucleotide sequence of SEQ ID NO: 4.

8. A cultured cell transformed with the vector of claim 5.

9. A process for making a modified thrombomodulin polypeptide comprising the steps of:
   cultivating the cell of claim 8 under conditions which permit the expression of the heterologous DNA, and
   collecting the polypeptides produced by said cell.

* * * * *

UNITED STATES PATENT AND TRADEMARK OFFICE
CERTIFICATE OF CORRECTION

PATENT NO. : 5,354,664
DATED : OCTOBER 11, 1994
INVENTOR(S) : TAKESHI DOI ET AL

It is certified that error appears in the above-identified patent and that said Letters Patent is hereby corrected as shown below:

Column 39, line 60, "$Xaa^{472}$ are arbitrary" should read --$Xaa^{476}$ are arbitrary--;
  line 63, "$Glu^{472}$." should read --$Glu^{476}$.--;
  line 66, "$Asp^{472}$." should read --$Asp^{476}$.--;

Column 40, line 64, after "according to claim 1;" insert
  --a termination codon; and
  a polyA addition signal.--;
  lines 65-70 should read as --7. A DNA molecule having the nucleotide sequence of SEQ ID NO:4.--

Signed and Sealed this

Sixteenth Day of May, 1995

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 476 amino acids
( B ) TYPE: amino acid
( D ) TOPOLOGY: linear ( i i ) MOLECULE TYPE: protein ( x i ) SEQUENCE DESCRIPTION: SEQ ID NO:1:

```
Ala Pro Ala Glu Pro Gln Pro Gly Gly Ser Gln Cys Val Glu His Asp
 1               5                  10                   15

Cys Phe Ala Leu Tyr Pro Gly Pro Ala Thr Phe Leu Asn Ala Ser Gln
                20                  25                  30

Ile Cys Asp Gly Leu Arg Gly His Leu Met Thr Val Arg Ser Ser Val
            35                  40                  45

Ala Ala Asp Val Ile Ser Leu Leu Asn Gly Asp Gly Val Gly
        50                  55                  60

Arg Arg Arg Leu Trp Ile Gly Leu Gln Leu Pro Pro Gly Cys Gly Asp
65                      70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Gln Cys Glu Val Lys Ala
    130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Ala Val Ser Ile Thr Tyr Gly
                165                 170                 175

Thr Pro Phe Ala Ala Arg Gly Ala Asp Phe Gln Ala Leu Pro Val Gly
            180                 185                 190

Ser Ser Ala Ala Val Ala Pro Leu Gly Leu Gln Leu Met Cys Thr Ala
        195                 200                 205

Pro Pro Gly Ala Val Gln Gly His Trp Ala Arg Glu Ala Pro Gly Ala
    210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
    290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Asp Pro Cys Phe
            340                 345                 350
```

-continued

```
Arg  Ala  Asn  Cys  Glu  Tyr  Gln  Cys  Gln  Pro  Leu  Asn  Gln  Thr  Ser  Tyr
          355                      360                     365

Leu  Cys  Val  Cys  Ala  Glu  Gly  Phe  Ala  Pro  Ile  Pro  His  Glu  Pro  His
     370                 375                     380

Arg  Cys  Gln  Met  Phe  Cys  Asn  Gln  Thr  Ala  Cys  Pro  Ala  Asp  Cys  Asp
385                      390                     395                          400

Pro  Asn  Thr  Gln  Ala  Ser  Cys  Glu  Cys  Pro  Glu  Gly  Tyr  Ile  Leu  Asp
                405                      410                          415

Asp  Gly  Phe  Ile  Cys  Thr  Asp  Ile  Asp  Glu  Cys  Glu  Asn  Gly  Gly  Phe
               420                      425                     430

Cys  Ser  Gly  Val  Cys  His  Asn  Leu  Pro  Gly  Thr  Phe  Glu  Cys  Ile  Cys
          435                 440                     445

Gly  Pro  Asp  Ser  Ala  Leu  Val  Arg  His  Ile  Gly  Thr  Asp  Cys  Asp  Ser
     450                 455                     460

Gly  Lys  Val  Asp  Glu  Asp  Tyr  Ser  Gly  Ser  Gly  Glu
465                      470                     475
```

( 2 ) INFORMATION FOR SEQ ID NO:2:

( i ) SEQUENCE CHARACTERISTICS:
( A ) LENGTH: 476 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Ala  Pro  Ala  Glu  Pro  Gln  Pro  Gly  Gly  Ser  Gln  Cys  Val  Glu  His  Asp
1                   5                   10                      15

Cys  Phe  Ala  Leu  Tyr  Pro  Gly  Pro  Ala  Thr  Phe  Leu  Asn  Ala  Ser  Gln
               20                      25                      30

Ile  Cys  Asp  Gly  Leu  Arg  Gly  His  Leu  Met  Thr  Val  Arg  Ser  Ser  Val
          35                 40                      45

Ala  Ala  Asp  Val  Ile  Ser  Leu  Leu  Leu  Asn  Gly  Asp  Gly  Gly  Val  Gly
     50                  55                      60

Arg  Arg  Arg  Leu  Trp  Ile  Gly  Leu  Gln  Leu  Pro  Pro  Gly  Cys  Gly  Asp
65                       70                      75                          80

Pro  Lys  Arg  Leu  Gly  Pro  Leu  Arg  Gly  Phe  Gln  Trp  Val  Thr  Gly  Asp
                85                      90                          95

Asn  Asn  Thr  Ser  Tyr  Ser  Arg  Trp  Ala  Arg  Leu  Asp  Leu  Asn  Gly  Ala
                100                     105                     110

Pro  Leu  Cys  Gly  Pro  Leu  Cys  Val  Ala  Val  Ser  Ala  Ala  Glu  Ala  Thr
          115                     120                     125

Val  Pro  Ser  Glu  Pro  Ile  Trp  Glu  Glu  Gln  Gln  Cys  Glu  Val  Lys  Ala
     130                     135                     140

Asp  Gly  Phe  Leu  Cys  Glu  Phe  His  Phe  Pro  Ala  Thr  Cys  Arg  Pro  Leu
145                     150                     155                          160

Ala  Val  Glu  Pro  Gly  Ala  Ala  Ala  Ala  Val  Ser  Ile  Thr  Tyr  Gly
                165                     170                     175

Thr  Pro  Phe  Ala  Ala  Arg  Gly  Ala  Asp  Phe  Gln  Ala  Leu  Pro  Val  Gly
               180                     185                     190

Ser  Ser  Ala  Ala  Val  Ala  Pro  Leu  Gly  Leu  Gln  Leu  Met  Cys  Thr  Ala
          195                     200                     205

Pro  Pro  Gly  Ala  Val  Gln  Gly  His  Trp  Ala  Arg  Glu  Ala  Pro  Gly  Ala
     210                     215                     220

Trp  Asp  Cys  Ser  Val  Glu  Asn  Gly  Gly  Cys  Glu  His  Ala  Cys  Asn  Ala
225                      230                     235                         240

Ile  Pro  Gly  Ala  Pro  Arg  Cys  Gln  Cys  Pro  Ala  Gly  Ala  Ala  Leu  Gln
```

|     | 245 |     |     |     |     | 250 |     |     |     |     | 255 |     |     |
|-----|-----|-----|-----|-----|-----|-----|-----|-----|-----|-----|-----|-----|-----|

Ala Asp Gly Arg Ser Cys Thr Ala Ser Ala Thr Gln Ser Cys Asn Asp
                260                     265                 270

Leu Cys Glu His Phe Cys Val Pro Asn Pro Asp Gln Pro Gly Ser Tyr
            275             280                 285

Ser Cys Met Cys Glu Thr Gly Tyr Arg Leu Ala Ala Asp Gln His Arg
        290                 295                 300

Cys Glu Asp Val Asp Asp Cys Ile Leu Glu Pro Ser Pro Cys Pro Gln
305                     310                 315                 320

Arg Cys Val Asn Thr Gln Gly Gly Phe Glu Cys His Cys Tyr Pro Asn
                325                     330                 335

Tyr Asp Leu Val Asp Gly Glu Cys Val Glu Pro Val Asp Pro Cys Phe
            340                 345                 350

Arg Ala Asn Cys Glu Tyr Gln Cys Gln Pro Leu Asn Gln Thr Ser Tyr
            355                 360                 365

Leu Cys Val Cys Ala Glu Gly Phe Ala Pro Ile Pro His Glu Pro His
    370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
                405                 410                 415

Asp Gly Phe Ile Cys Thr Asp Ile Asp Glu Cys Glu Asn Gly Gly Phe
            420                 425                 430

Cys Ser Gly Val Cys His Asn Leu Pro Gly Thr Phe Glu Cys Ile Cys
        435                 440                 445

Gly Pro Asp Ser Ala Leu Val Arg His Ile Gly Thr Asp Cys Asp Ser
    450                 455                 460

Gly Lys Val Asp Asp Glu Ala Ser Gly Ser Gly Asp
465                 470                 475

( 2 ) INFORMATION FOR SEQ ID NO:3:

( i ) SEQUENCE CHARACTERISTICS:
( A ) LENGTH: 1428 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO:3:

| | | | | | |
|---|---|---|---|---|---|
| GCACCCGCAG | AGCCGCAGCC | GGGTGGCAGC | CAGTGCGTCG | AGCACGACTG | CTTCGCGCTC | 60 |
| TACCCGGGCC | CCGCGACCTT | CCTCAATGCC | AGTCAGATCT | GCGACGGACT | GCGGGGCCAC | 120 |
| CTAATGACAG | TGCGCTCCTC | GGTGGCTGCC | GATGTCATTT | CCTTGCTACT | GAACGGCGAC | 180 |
| GGCGGCGTTG | GCCGCCGGCG | CCTCTGGATC | GGCCTGCAGC | TGCCACCCGG | CTGCGGCGAC | 240 |
| CCCAAGCGCC | TCGGGCCCCT | GCGCGGCTTC | CAGTGGGTTA | CGGGAGACAA | CAACACCAGC | 300 |
| TATAGCAGGT | GGGCACGGCT | CGACCTCAAT | GGGGCTCCCC | TCTGCGGCCC | GTTGTGCGTC | 360 |
| GCTGTCTCCG | CTGCTGAGGC | CACTGTGCCC | AGCGAGCCGA | TCTGGGAGGA | GCAGCAGTGC | 420 |
| GAAGTGAAGG | CCGATGGCTT | CCTCTGCGAG | TTCCACTTCC | CAGCCACCTG | CAGGCCACTG | 480 |
| GCTGTGGAGC | CCGGCGCCGC | GGCTGCCGCC | GTCTCGATCA | CCTACGGCAC | CCCGTTCGCG | 540 |
| GCCCGCGGAG | CGGACTTCCA | GGCGCTGCCG | GTGGGCAGCT | CCGCCGCGGT | GGCTCCCCTC | 600 |
| GGCTTACAGC | TAATGTGCAC | CGCGCCGCCC | GGAGCGGTCC | AGGGGCACTG | GCCAGGGAG | 660 |
| GCGCCGGGCG | CTTGGGACTG | CAGCGTGGAG | AACGGCGGCT | GCGAGCACGC | GTGCAATGCG | 720 |
| ATCCCTGGGG | CTCCCCGCTG | CCAGTGCCCA | GCCGGCGCCG | CCCTGCAGGC | AGACGGGCGC | 780 |

| | | | | | |
|---|---|---|---|---|---|
| TCCTGCACCG | CATCCGCGAC | GCAGTCCTGC | AACGACCTCT | GCGAGCACTT | CTGCGTTCCC | 840 |
| AACCCCGACC | AGCCGGGCTC | CTACTCGTGC | ATGTGCGAGA | CCGGCTACCG | GCTGGCGGCC | 900 |
| GACCAACACC | GGTGCGAGGA | CGTGGATGAC | TGCATACTGG | AGCCCAGTCC | GTGTCCGCAG | 960 |
| CGCTGTGTCA | ACACACAGGG | TGGCTTCGAG | TGCCACTGCT | ACCCTAACTA | CGACCTGGTG | 1020 |
| GACGGCGAGT | GTGTGGAGCC | CGTGGACCCG | TGCTTCAGAG | CCAACTGCGA | GTACCAGTGC | 1080 |
| CAGCCCCTGA | ACCAAACTAG | CTACCTCTGC | GTCTGCGCCG | AGGGCTTCGC | GCCCATTCCC | 1140 |
| CACGAGCCGC | ACAGGTGCCA | GATGTTTTGC | AACCAGACTG | CCTGTCCAGC | CGACTGCGAC | 1200 |
| CCCAACACCC | AGGCTAGCTG | TGAGTGCCCT | GAAGGCTACA | TCCTGGACGA | CGGTTTCATC | 1260 |
| TGCACGGACA | TCGACGAGTG | CGAAAACGGC | GGCTTCTGCT | CCGGGGTGTG | CCACAACCTC | 1320 |
| CCCGGTACCT | TCGAGTGCAT | CTGCGGGCCC | GACTCGGCCC | TTGTCCGCCA | CATTGGCACC | 1380 |
| GACTGTGACT | CCGGCAAGGT | GGACGAGGAC | TATAGCGGCT | CTGGCGAG | | 1428 |

( 2 ) INFORMATION FOR SEQ ID NO:4:

( i ) SEQUENCE CHARACTERISTICS:
        ( A ) LENGTH: 1428 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:4:

| | | | | | |
|---|---|---|---|---|---|
| GCACCCGCAG | AGCCGCAGCC | GGGTGGCAGC | CAGTGCGTCG | AGCACGACTG | CTTCGCGCTC | 60 |
| TACCGGGCC | CCGCGACCTT | CCTCAATGCC | AGTCAGATCT | GCGACGGACT | GCGGGGCCAC | 120 |
| CTAATGACAG | TGCGCTCCTC | GGTGGCTGCC | GATGTCATTT | CCTTGCTACT | GAACGGCGAC | 180 |
| GGCGGCGTTG | GCCGCCGGCG | CCTCTGGATC | GGCCTGCAGC | TGCCACCCGG | CTGCGGCGAC | 240 |
| CCCAAGCGCC | TCGGGCCCCT | GCGCGGCTTC | CAGTGGGTTA | CGGGAGACAA | CAACACCAGC | 300 |
| TATAGCAGGT | GGGCACGGCT | CGACCTCAAT | GGGGCTCCCC | TCTGCGGCCC | GTTGTGCGTC | 360 |
| GCTGTCTCCG | CTGCTGAGGC | CACTGTGCCC | AGCGAGCCGA | TCTGGGAGGA | GCAGCAGTGC | 420 |
| GAAGTGAAGG | CCGATGGCTT | CCTCTGCGAG | TTCCACTTCC | CAGCCACCTG | CAGGCCACTG | 480 |
| GCTGTGGAGC | CCGGCGCCGC | GGCTGCCGCC | GTCTCGATCA | CCTACGGCAC | CCCGTTCGCG | 540 |
| GCCCGCGGAG | CGGACTTCCA | GGCGCTGCCG | GTGGGCAGCT | CCGCCGCGGT | GGCTCCCCTC | 600 |
| GGCTTACAGC | TAATGTGCAC | CGCGCCGCCC | GGAGCGGTCC | AGGGGCACTG | GGCCAGGGAG | 660 |
| GCGCCGGGCG | CTTGGGACTG | CAGCGTGGAG | AACGGCGGCT | GCGAGCACGC | GTGCAATGCG | 720 |
| ATCCCTGGGG | CTCCCCGCTG | CCAGTGCCCA | GCCGGCGCCG | CCCTGCAGGC | AGACGGGCGC | 780 |
| TCCTGCACCG | CATCCGCGAC | GCAGTCCTGC | AACGACCTCT | GCGAGCACTT | CTGCGTTCCC | 840 |
| AACCCCGACC | AGCCGGGCTC | CTACTCGTGC | ATGTGCGAGA | CCGGCTACCG | GCTGGCGGCC | 900 |
| GACCAACACC | GGTGCGAGGA | CGTGGATGAC | TGCATACTGG | AGCCCAGTCC | GTGTCCGCAG | 960 |
| CGCTGTGTCA | ACACACAGGG | TGGCTTCGAG | TGCCACTGCT | ACCCTAACTA | CGACCTGGTG | 1020 |
| GACGGCGAGT | GTGTGGAGCC | CGTGGACCCG | TGCTTCAGAG | CCAACTGCGA | GTACCAGTGC | 1080 |
| CAGCCCCTGA | ACCAAACTAG | CTACCTCTGC | GTCTGCGCCG | AGGGCTTCGC | GCCCATTCCC | 1140 |
| CACGAGCCGC | ACAGGTGCCA | GATGTTTTGC | AACCAGACTG | CCTGTCCAGC | CGACTGCGAC | 1200 |
| CCCAACACCC | AGGCTAGCTG | TGAGTGCCCT | GAAGGCTACA | TCCTGGACGA | CGGTTTCATC | 1260 |
| TGCACGGACA | TCGACGAGTG | CGAAAACGGC | GGCTTCTGCT | CCGGGGTGTG | CCACAACCTC | 1320 |
| CCCGGTACCT | TCGAGTGCAT | CTGCGGGCCC | GACTCGGCCC | TTGTCCGCCA | CATTGGCACC | 1380 |

GACTGTGACT CCGGCAAGGT CGACGACGAG GCCAGCGGCT CTGGCGAC              1428

( 2 ) INFORMATION FOR SEQ ID NO:5:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: DNA (synthetic)

( x i ) SEQUENCE DESCRIPTION: SEQ ID NO:5:

AGGGCCGGGC ACTTATAAAC T                                          21

( 2 ) INFORMATION FOR SEQ ID NO:6:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: DNA (synthetic)

( x i ) SEQUENCE DESCRIPTION: SEQ ID NO:6:

CCCAGTGGTC CAGTGACGTC A                                          21

( 2 ) INFORMATION FOR SEQ ID NO:7:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: DNA (synthetic)

( x i ) SEQUENCE DESCRIPTION: SEQ ID NO:7:

CTTCGAGTGC ATCTGCGGGC CCGACTCGGC CCTTGTCCG                       39

( 2 ) INFORMATION FOR SEQ ID NO:8:

( i ) SEQUENCE CHARACTERISTICS:
        ( A ) LENGTH: 49 bases
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: DNA (synthetic)

( x i ) SEQUENCE DESCRIPTION: SEQ ID NO:8:

ATGTGGCGGA CAAGGGCCGA GTCGGGCCCG CAGATGCACT CGAAGGTAC            49

( 2 ) INFORMATION FOR SEQ ID NO:9:

( i ) SEQUENCE CHARACTERISTICS:
        ( A ) LENGTH: 65 bases
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: DNA (synthetic)

( x i ) SEQUENCE DESCRIPTION: SEQ ID NO:9:

CCACATTGGC ACCGACTGTG ACTCCGGCAA GGTGGACGAG GACTATAGCG GCTCTGGCGA   60

GTGAC 65

( 2 ) INFORMATION FOR SEQ ID NO:10:

( i ) SEQUENCE CHARACTERISTICS:
        ( A ) LENGTH: 63 bases
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: DNA (synthetic)

( x i ) SEQUENCE DESCRIPTION: SEQ ID NO:10:

TCGAGTCACT CGCCAGAGCC GCTATAGTCC TCGTCCACCT TGCCGGAGTC ACAGTCGGTG 60

CCA 63

( 2 ) INFORMATION FOR SEQ ID NO:11:

( i ) SEQUENCE CHARACTERISTICS:
        ( A ) LENGTH: 65 bases
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: DNA (synthetic)

( x i ) SEQUENCE DESCRIPTION: SEQ ID NO:11:

CCACATTGGC ACCGACTGTG ACTCCGGCAA GGTCGACGAC GAGGCCAGCG GCTCTGGCGA 60

CTGAC 65

( 2 ) INFORMATION FOR SEQ ID NO:12:

( i ) SEQUENCE CHARACTERISTICS:
        ( A ) LENGTH: 63 bases
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: DNA (synthetic)

( x i ) SEQUENCE DESCRIPTION: SEQ ID NO:12:

TCGAGTCAGT CGCCAGAGCC GCTGGCCTCG TCGTCGACCT TGCCGGAGTC ACAGTCGGTG 60

CCA 63

( 2 ) INFORMATION FOR SEQ ID NO:13:

( i ) SEQUENCE CHARACTERISTICS:
        ( A ) LENGTH: 1680 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: sigpeptide
        ( B ) LOCATION: 190..243

( i x ) FEATURE:
        ( A ) NAME/KEY: CDS
        ( B ) LOCATION: 190..1671

( i x ) FEATURE:
        ( A ) NAME/KEY: matpeptide
        ( B ) LOCATION: 244..1671

( x i ) SEQUENCE DESCRIPTION: SEQ ID NO:13:

CTCGAGCCCT GGCCGATCCG CATGTCAGAG GCTGCCTCGC AGGGGCTGCG CGCAGCGGCA 60

-continued

| | | |
|---|---|---|
| AGAAGTGTCT GGGCTGGGAC GGACAGGAGA GGCTGTCGCC ATCGGCGTCC TGTGCCCCTC | | 120 |
| TGCTCCGGCA CGGCCCTGTC GCAGTGCCCG CGCTTTCCCC GGCGCCTGCA CGCGGCGCGC | | 180 |
| CTGGGTAAC ATG CTT GGG GTC CTG GTC CTT GGC GCG CTG GCC CTG GCC | | 228 |
| Met Leu Gly Val Leu Val Leu Gly Ala Leu Ala Leu Ala | | |
| -18       -15                      -10 | | |

```
GGC CTG GGG TTC CCC GCA CCC GCA GAG CCG CAG CCG GGT GGC AGC CAG        276
Gly Leu Gly Phe Pro Ala Pro Ala Glu Pro Gln Pro Gly Gly Ser Gln
 -5                1               5                      10

TGC GTC GAG CAC GAC TGC TTC GCG CTC TAC CCG GGC CCC GCG ACC TTC        324
Cys Val Glu His Asp Cys Phe Ala Leu Tyr Pro Gly Pro Ala Thr Phe
             15              20                  25

CTC AAT GCC AGT CAG ATC TGC GAC GGA CTG CGG GGC CAC CTA ATG ACA        372
Leu Asn Ala Ser Gln Ile Cys Asp Gly Leu Arg Gly His Leu Met Thr
         30              35                  40

GTG CGC TCC TCG GTG GCT GCC GAT GTC ATT TCC TTG CTA CTG AAC GGC        420
Val Arg Ser Ser Val Ala Ala Asp Val Ile Ser Leu Leu Leu Asn Gly
     45              50              55

GAC GGC GGC GTT GGC CGC CGG CGC CTC TGG ATC GGC CTG CAG CTG CCA        468
Asp Gly Gly Val Gly Arg Arg Arg Leu Trp Ile Gly Leu Gln Leu Pro
 60              65              70                  75

CCC GGC TGC GGC GAC CCC AAG CGC CTC GGG CCC CTG CGC GGC TTC CAG        516
Pro Gly Cys Gly Asp Pro Lys Arg Leu Gly Pro Leu Arg Gly Phe Gln
                 80              85                  90

TGG GTT ACG GGA GAC AAC AAC ACC AGC TAT AGC AGG TGG GCA CGG CTC        564
Trp Val Thr Gly Asp Asn Asn Thr Ser Tyr Ser Arg Trp Ala Arg Leu
             95              100                 105

GAC CTC AAT GGG GCT CCC CTC TGC GGC CCG TTG TGC GTC GCT GTC TCC        612
Asp Leu Asn Gly Ala Pro Leu Cys Gly Pro Leu Cys Val Ala Val Ser
         110             115                 120

GCT GCT GAG GCC ACT GTG CCC AGC GAG CCG ATC TGG GAG GAG CAG CAG        660
Ala Ala Glu Ala Thr Val Pro Ser Glu Pro Ile Trp Glu Glu Gln Gln
     125             130                 135

TGC GAA GTG AAG GCC GAT GGC TTC CTC TGC GAG TTC CAC TTC CCA GCC        708
Cys Glu Val Lys Ala Asp Gly Phe Leu Cys Glu Phe His Phe Pro Ala
140              145                 150                 155

ACC TGC AGG CCA CTG GCT GTG GAG CCC GGC GCC GCG GCT GCC GCC GTC        756
Thr Cys Arg Pro Leu Ala Val Glu Pro Gly Ala Ala Ala Ala Ala Val
                 160             165                 170

TCG ATC ACC TAC GGC ACC CCG TTC GCG GCC CGC GGA GCG GAC TTC CAG        804
Ser Ile Thr Tyr Gly Thr Pro Phe Ala Ala Arg Gly Ala Asp Phe Gln
             175             180                 185

GCG CTG CCG GTG GGC AGC TCC GCC GCG GTG GCT CCC CTC GGC TTA CAG        852
Ala Leu Pro Val Gly Ser Ser Ala Ala Val Ala Pro Leu Gly Leu Gln
         190             195                 200

CTA ATG TGC ACC GCG CCG CCC GGA GCG GTC CAG GGG CAC TGG GCC AGG        900
Leu Met Cys Thr Ala Pro Pro Gly Ala Val Gln Gly His Trp Ala Arg
     205             210                 215

GAG GCG CCG GGC GCT TGG GAC TGC AGC GTG GAG AAC GGC GGC TGC GAG        948
Glu Ala Pro Gly Ala Trp Asp Cys Ser Val Glu Asn Gly Gly Cys Glu
220              225                 230                 235

CAC GCG TGC AAT GCG ATC CCT GGG GCT CCC CGC TGC CAG TGC CCA GCC        996
His Ala Cys Asn Ala Ile Pro Gly Ala Pro Arg Cys Gln Cys Pro Ala
                 240             245                 250

GGC GCC GCC CTG CAG GCA GAC GGG CGC TCC TGC ACC GCA TCC GCG ACG       1044
Gly Ala Ala Leu Gln Ala Asp Gly Arg Ser Cys Thr Ala Ser Ala Thr
             255             260                 265

CAG TCC TGC AAC GAC CTC TGC GAG CAC TTC TGC GTT CCC AAC CCC GAC       1092
Gln Ser Cys Asn Asp Leu Cys Glu His Phe Cys Val Pro Asn Pro Asp
         270             275                 280
```

| | | | | | | | | | | | | | | | | |
|---|---|---|---|---|---|---|---|---|---|---|---|---|---|---|---|---|
| CAG | CCG | GGC | TCC | TAC | TCG | TGC | ATG | TGC | GAG | ACC | GGC | TAC | CGG | CTG | GCG | 1140 |
| Gln | Pro | Gly | Ser | Tyr | Ser | Cys | Met | Cys | Glu | Thr | Gly | Tyr | Arg | Leu | Ala | |
| | 285 | | | | 290 | | | | | 295 | | | | | | |
| GCC | GAC | CAA | CAC | CGG | TGC | GAG | GAC | GTG | GAT | GAC | TGC | ATA | CTG | GAG | CCC | 1188 |
| Ala | Asp | Gln | His | Arg | Cys | Glu | Asp | Val | Asp | Asp | Cys | Ile | Leu | Glu | Pro | |
| 300 | | | | | 305 | | | | 310 | | | | | | 315 | |
| AGT | CCG | TGT | CCG | CAG | CGC | TGT | GTC | AAC | ACA | CAG | GGT | GGC | TTC | GAG | TGC | 1236 |
| Ser | Pro | Cys | Pro | Gln | Arg | Cys | Val | Asn | Thr | Gln | Gly | Gly | Phe | Glu | Cys | |
| | | | | 320 | | | | | 325 | | | | | 330 | | |
| CAC | TGC | TAC | CCT | AAC | TAC | GAC | CTG | GTG | GAC | GGC | GAG | TGT | GTG | GAG | CCC | 1284 |
| His | Cys | Tyr | Pro | Asn | Tyr | Asp | Leu | Val | Asp | Gly | Glu | Cys | Val | Glu | Pro | |
| | | | 335 | | | | | 340 | | | | 345 | | | | |
| GTG | GAC | CCG | TGC | TTC | AGA | GCC | AAC | TGC | GAG | TAC | CAG | TGC | CAG | CCC | CTG | 1332 |
| Val | Asp | Pro | Cys | Phe | Arg | Ala | Asn | Cys | Glu | Tyr | Gln | Cys | Gln | Pro | Leu | |
| | | 350 | | | | | 355 | | | | | 360 | | | | |
| AAC | CAA | ACT | AGC | TAC | CTC | TGC | GTC | TGC | GCC | GAG | GGC | TTC | GCG | CCC | ATT | 1380 |
| Asn | Gln | Thr | Ser | Tyr | Leu | Cys | Val | Cys | Ala | Glu | Gly | Phe | Ala | Pro | Ile | |
| | 365 | | | | | 370 | | | | | 375 | | | | | |
| CCC | CAC | GAG | CCG | CAC | AGG | TGC | CAG | ATG | TTT | TGC | AAC | CAG | ACT | GCC | TGT | 1428 |
| Pro | His | Glu | Pro | His | Arg | Cys | Gln | Met | Phe | Cys | Asn | Gln | Thr | Ala | Cys | |
| 380 | | | | | 385 | | | | | 390 | | | | | 395 | |
| CCA | GCC | GAC | TGC | GAC | CCC | AAC | ACC | CAG | GCT | AGC | TGT | GAG | TGC | CCT | GAA | 1476 |
| Pro | Ala | Asp | Cys | Asp | Pro | Asn | Thr | Gln | Ala | Ser | Cys | Glu | Cys | Pro | Glu | |
| | | | | 400 | | | | | 405 | | | | | 410 | | |
| GGC | TAC | ATC | CTG | GAC | GAC | GGT | TTC | ATC | TGC | ACG | GAC | ATC | GAC | GAG | TGC | 1524 |
| Gly | Tyr | Ile | Leu | Asp | Asp | Gly | Phe | Ile | Cys | Thr | Asp | Ile | Asp | Glu | Cys | |
| | | | 415 | | | | | 420 | | | | | 425 | | | |
| GAA | AAC | GGC | GGC | TTC | TGC | TCC | GGG | GTG | TGC | CAC | AAC | CTC | CCC | GGT | ACC | 1572 |
| Glu | Asn | Gly | Gly | Phe | Cys | Ser | Gly | Val | Cys | His | Asn | Leu | Pro | Gly | Thr | |
| | | | 430 | | | | | 435 | | | | | 440 | | | |
| TTC | GAG | TGC | ATC | TGC | GGG | CCC | GAC | TCG | GCC | CTT | GTC | CGC | CAC | ATT | GGC | 1620 |
| Phe | Glu | Cys | Ile | Cys | Gly | Pro | Asp | Ser | Ala | Leu | Val | Arg | His | Ile | Gly | |
| | | 445 | | | | | 450 | | | | | 455 | | | | |
| ACC | GAC | TGT | GAC | TCC | GGC | AAG | GTG | GAC | GAG | GAC | TAT | AGC | GGC | TCT | GGC | 1668 |
| Thr | Asp | Cys | Asp | Ser | Gly | Lys | Val | Asp | Glu | Asp | Tyr | Ser | Gly | Ser | Gly | |
| 460 | | | | | 465 | | | | | 470 | | | | | 475 | |
| GAG | TGACTCGAG | | | | | | | | | | | | | | | 1680 |
| Glu | | | | | | | | | | | | | | | | |

(2) INFORMATION FOR SEQ ID NO:14:

(i) SEQUENCE CHARACTERISTICS:
        (A) LENGTH: 494 amino acids
        (B) TYPE: amino acid
        (D) TOPOLOGY: linear (ii) MOLECULE TYPE: protein (xi) SEQUENCE DESCRIPTION: SEQ ID NO:14:

| | | | | | | | | | | | | | | |
|---|---|---|---|---|---|---|---|---|---|---|---|---|---|---|
| Met | Leu | Gly | Val | Leu | Val | Leu | Gly | Ala | Leu | Ala | Leu | Ala | Gly | Leu | Gly |
| -18 | | | -15 | | | | | -10 | | | | | -5 | | |
| Phe | Pro | Ala | Pro | Ala | Glu | Pro | Gln | Pro | Gly | Gly | Ser | Gln | Cys | Val | Glu |
| | 1 | | | | 5 | | | | | 10 | | | | | |
| His | Asp | Cys | Phe | Ala | Leu | Tyr | Pro | Gly | Pro | Ala | Thr | Phe | Leu | Asn | Ala |
| 15 | | | | | 20 | | | | | 25 | | | | | 30 |
| Ser | Gln | Ile | Cys | Asp | Gly | Leu | Arg | Gly | His | Leu | Met | Thr | Val | Arg | Ser |
| | | | 35 | | | | | 40 | | | | | 45 | | |
| Ser | Val | Ala | Ala | Asp | Val | Ile | Ser | Leu | Leu | Leu | Asn | Gly | Asp | Gly | Gly |
| | | | 50 | | | | | 55 | | | | | 60 | | |
| Val | Gly | Arg | Arg | Arg | Leu | Trp | Ile | Gly | Leu | Gln | Leu | Pro | Pro | Gly | Cys |
| | | 65 | | | | | 70 | | | | | 75 | | | |
| Gly | Asp | Pro | Lys | Arg | Leu | Gly | Pro | Leu | Arg | Gly | Phe | Gln | Trp | Val | Thr |

```
         80                          85                          90
Gly  Asp  Asn  Asn  Thr  Ser  Tyr  Ser  Arg  Trp  Ala  Arg  Leu  Asp  Leu  Asn
 95                      100                     105                     110

Gly  Ala  Pro  Leu  Cys  Gly  Pro  Leu  Cys  Val  Ala  Val  Ser  Ala  Ala  Glu
                    115                     120                     125

Ala  Thr  Val  Pro  Ser  Glu  Pro  Ile  Trp  Glu  Glu  Gln  Gln  Cys  Glu  Val
               130                     135                          140

Lys  Ala  Asp  Gly  Phe  Leu  Cys  Glu  Phe  His  Phe  Pro  Ala  Thr  Cys  Arg
               145                     150                     155

Pro  Leu  Ala  Val  Glu  Pro  Gly  Ala  Ala  Ala  Ala  Ala  Val  Ser  Ile  Thr
          160                     165                     170

Tyr  Gly  Thr  Pro  Phe  Ala  Ala  Arg  Gly  Ala  Asp  Phe  Gln  Ala  Leu  Pro
175                      180                     185                          190

Val  Gly  Ser  Ser  Ala  Ala  Val  Ala  Pro  Leu  Gly  Leu  Gln  Leu  Met  Cys
               195                     200                     205

Thr  Ala  Pro  Pro  Gly  Ala  Val  Gln  Gly  His  Trp  Ala  Arg  Glu  Ala  Pro
               210                     215                     220

Gly  Ala  Trp  Asp  Cys  Ser  Val  Glu  Asn  Gly  Gly  Cys  Glu  His  Ala  Cys
               225                     230                     235

Asn  Ala  Ile  Pro  Gly  Ala  Pro  Arg  Cys  Gln  Cys  Pro  Ala  Gly  Ala  Ala
          240                     245                     250

Leu  Gln  Ala  Asp  Gly  Arg  Ser  Cys  Thr  Ala  Ser  Ala  Thr  Gln  Ser  Cys
255                      260                     265                          270

Asn  Asp  Leu  Cys  Glu  His  Phe  Cys  Val  Pro  Asn  Pro  Asp  Gln  Pro  Gly
               275                     280                     285

Ser  Tyr  Ser  Cys  Met  Cys  Glu  Thr  Gly  Tyr  Arg  Leu  Ala  Ala  Asp  Gln
               290                     295                     300

His  Arg  Cys  Glu  Asp  Val  Asp  Asp  Cys  Ile  Leu  Glu  Pro  Ser  Pro  Cys
          305                     310                     315

Pro  Gln  Arg  Cys  Val  Asn  Thr  Gln  Gly  Gly  Phe  Glu  Cys  His  Cys  Tyr
     320                     325                     330

Pro  Asn  Tyr  Asp  Leu  Val  Asp  Gly  Glu  Cys  Val  Glu  Pro  Val  Asp  Pro
335                      340                     345                          350

Cys  Phe  Arg  Ala  Asn  Cys  Glu  Tyr  Gln  Cys  Gln  Pro  Leu  Asn  Gln  Thr
               355                     360                     365

Ser  Tyr  Leu  Cys  Val  Cys  Ala  Glu  Gly  Phe  Ala  Pro  Ile  Pro  His  Glu
               370                     375                     380

Pro  His  Arg  Cys  Gln  Met  Phe  Cys  Asn  Gln  Thr  Ala  Cys  Pro  Ala  Asp
          385                     390                     395

Cys  Asp  Pro  Asn  Thr  Gln  Ala  Ser  Cys  Glu  Cys  Pro  Glu  Gly  Tyr  Ile
     400                     405                     410

Leu  Asp  Asp  Gly  Phe  Ile  Cys  Thr  Asp  Ile  Asp  Glu  Cys  Glu  Asn  Gly
415                      420                     425                          430

Gly  Phe  Cys  Ser  Gly  Val  Cys  His  Asn  Leu  Pro  Gly  Thr  Phe  Glu  Cys
               435                     440                     445

Ile  Cys  Gly  Pro  Asp  Ser  Ala  Leu  Val  Arg  His  Ile  Gly  Thr  Asp  Cys
               450                     455                     460

Asp  Ser  Gly  Lys  Val  Asp  Glu  Asp  Tyr  Ser  Gly  Ser  Gly  Glu
               465                     470                     475
```

( 2 ) INFORMATION FOR SEQ ID NO:15:

( i ) SEQUENCE CHARACTERISTICS:
        ( A ) LENGTH: 1680 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
 ( A ) NAME/KEY: sigpeptide
 ( B ) LOCATION: 190..243

( i x ) FEATURE:
 ( A ) NAME/KEY: CDS
 ( B ) LOCATION: 190..1671

( i x ) FEATURE:
 ( A ) NAME/KEY: matpeptide
 ( B ) LOCATION: 244..1671

( x i ) SEQUENCE DESCRIPTION: SEQ ID NO:15:

```
CTCGAGCCCT GGCCGATCCG CATGTCAGAG GCTGCCTCGC AGGGGCTGCG CGCAGCGGCA        60

AGAAGTGTCT GGGCTGGGAC GGACAGGAGA GGCTGTCGCC ATCGGCGTCC TGTGCCCCTC       120

TGCTCCGGCA CGGCCCTGTC GCAGTGCCCG CGCTTTCCCC GGCGCCTGCA CGCGGCGCGC       180

CTGGGTAAC ATG CTT GGG GTC CTG GTC CTT GGC GCG CTG GCC CTG GCC           228
          Met Leu Gly Val Leu Val Leu Gly Ala Leu Ala Leu Ala
          -18         -15                 -10

GGC CTG GGG TTC CCC GCA CCC GCA GAG CCG CAG CCG GGT GGC AGC CAG         276
Gly Leu Gly Phe Pro Ala Pro Ala Glu Pro Gln Pro Gly Gly Ser Gln
-5                1               5                   10

TGC GTC GAG CAC GAC TGC TTC GCG CTC TAC CCG GGC CCC GCG ACC TTC         324
Cys Val Glu His Asp Cys Phe Ala Leu Tyr Pro Gly Pro Ala Thr Phe
             15                  20                  25

CTC AAT GCC AGT CAG ATC TGC GAC GGA CTG CGG GGC CAC CTA ATG ACA         372
Leu Asn Ala Ser Gln Ile Cys Asp Gly Leu Arg Gly His Leu Met Thr
             30              35                  40

GTG CGC TCC TCG GTG GCT GCC GAT GTC ATT TCC TTG CTA CTG AAC GGC         420
Val Arg Ser Ser Val Ala Ala Asp Val Ile Ser Leu Leu Leu Asn Gly
    45                  50                  55

GAC GGC GGC GTT GGC CGC CGG CGC CTC TGG ATC GGC CTG CAG CTG CCA         468
Asp Gly Gly Val Gly Arg Arg Arg Leu Trp Ile Gly Leu Gln Leu Pro
60                  65                  70                  75

CCC GGC TGC GGC GAC CCC AAG CGC CTC GGG CCC CTG CGC GGC TTC CAG         516
Pro Gly Cys Gly Asp Pro Lys Arg Leu Gly Pro Leu Arg Gly Phe Gln
                80                  85                  90

TGG GTT ACG GGA GAC AAC AAC ACC AGC TAT AGC AGG TGG GCA CGG CTC         564
Trp Val Thr Gly Asp Asn Asn Thr Ser Tyr Ser Arg Trp Ala Arg Leu
             95                  100                 105

GAC CTC AAT GGG GCT CCC CTC TGC GGC CCG TTG TGC GTC GCT GTC TCC         612
Asp Leu Asn Gly Ala Pro Leu Cys Gly Pro Leu Cys Val Ala Val Ser
         110                 115                 120

GCT GCT GAG GCC ACT GTG CCC AGC GAG CCG ATC TGG GAG GAG CAG CAG         660
Ala Ala Glu Ala Thr Val Pro Ser Glu Pro Ile Trp Glu Glu Gln Gln
125                 130                 135

TGC GAA GTG AAG GCC GAT GGC TTC CTC TGC GAG TTC CAC TTC CCA GCC         708
Cys Glu Val Lys Ala Asp Gly Phe Leu Cys Glu Phe His Phe Pro Ala
140                 145                 150                 155

ACC TGC AGG CCA CTG GCT GTG GAG CCC GGC GCC GCG GCT GCC GCC GTC         756
Thr Cys Arg Pro Leu Ala Val Glu Pro Gly Ala Ala Ala Ala Ala Val
                160                 165                 170

TCG ATC ACC TAC GGC ACC CCG TTC GCG GCC CGC GGA GCG GAC TTC CAG         804
Ser Ile Thr Tyr Gly Thr Pro Phe Ala Ala Arg Gly Ala Asp Phe Gln
             175                 180                 185

GCG CTG CCG GTG GGC AGC TCC GCC GCG GTG GCT CCC CTC GGC TTA CAG         852
Ala Leu Pro Val Gly Ser Ser Ala Ala Val Ala Pro Leu Gly Leu Gln
         190                 195                 200

CTA ATG TGC ACC GCG CCG CCC GGA GCG GTC CAG GGG CAC TGG GCC AGG         900
Leu Met Cys Thr Ala Pro Pro Gly Ala Val Gln Gly His Trp Ala Arg
```

-continued

|  | 205 |  |  |  | 210 |  |  |  | 215 |  |  |  |  |  |  |  |
|---|---|---|---|---|---|---|---|---|---|---|---|---|---|---|---|---|
| GAG | GCG | CCG | GGC | GCT | TGG | GAC | TGC | AGC | GTG | GAG | AAC | GGC | GGC | TGC | GAG | 948 |
| Glu | Ala | Pro | Gly | Ala | Trp | Asp | Cys | Ser | Val | Glu | Asn | Gly | Gly | Cys | Glu |  |
| 220 |  |  |  |  | 225 |  |  |  | 230 |  |  |  |  |  | 235 |  |
| CAC | GCG | TGC | AAT | GCG | ATC | CCT | GGG | GCT | CCC | CGC | TGC | CAG | TGC | CCA | GCC | 996 |
| His | Ala | Cys | Asn | Ala | Ile | Pro | Gly | Ala | Pro | Arg | Cys | Gln | Cys | Pro | Ala |  |
|  |  |  |  | 240 |  |  |  |  | 245 |  |  |  |  | 250 |  |  |
| GGC | GCC | GCC | CTG | CAG | GCA | GAC | GGG | CGC | TCC | TGC | ACC | GCA | TCC | GCG | ACG | 1044 |
| Gly | Ala | Ala | Leu | Gln | Ala | Asp | Gly | Arg | Ser | Cys | Thr | Ala | Ser | Ala | Thr |  |
|  |  |  |  | 255 |  |  |  |  | 260 |  |  |  |  | 265 |  |  |
| CAG | TCC | TGC | AAC | GAC | CTC | TGC | GAG | CAC | TTC | TGC | GTT | CCC | AAC | CCC | GAC | 1092 |
| Gln | Ser | Cys | Asn | Asp | Leu | Cys | Glu | His | Phe | Cys | Val | Pro | Asn | Pro | Asp |  |
|  |  | 270 |  |  |  |  | 275 |  |  |  |  | 280 |  |  |  |  |
| CAG | CCG | GGC | TCC | TAC | TCG | TGC | ATG | TGC | GAG | ACC | GGC | TAC | CGG | CTG | GCG | 1140 |
| Gln | Pro | Gly | Ser | Tyr | Ser | Cys | Met | Cys | Glu | Thr | Gly | Tyr | Arg | Leu | Ala |  |
|  | 285 |  |  |  |  | 290 |  |  |  |  | 295 |  |  |  |  |  |
| GCC | GAC | CAA | CAC | CGG | TGC | GAG | GAC | GTG | GAT | GAC | TGC | ATA | CTG | GAG | CCC | 1188 |
| Ala | Asp | Gln | His | Arg | Cys | Glu | Asp | Val | Asp | Asp | Cys | Ile | Leu | Glu | Pro |  |
| 300 |  |  |  |  | 305 |  |  |  |  | 310 |  |  |  |  | 315 |  |
| AGT | CCG | TGT | CCG | CAG | CGC | TGT | GTC | AAC | ACA | CAG | GGT | GGC | TTC | GAG | TGC | 1236 |
| Ser | Pro | Cys | Pro | Gln | Arg | Cys | Val | Asn | Thr | Gln | Gly | Gly | Phe | Glu | Cys |  |
|  |  |  |  | 320 |  |  |  |  | 325 |  |  |  |  | 330 |  |  |
| CAC | TGC | TAC | CCT | AAC | TAC | GAC | CTG | GTG | GAC | GGC | GAG | TGT | GTG | GAG | CCC | 1284 |
| His | Cys | Tyr | Pro | Asn | Tyr | Asp | Leu | Val | Asp | Gly | Glu | Cys | Val | Glu | Pro |  |
|  |  |  | 335 |  |  |  |  | 340 |  |  |  |  | 345 |  |  |  |
| GTG | GAC | CCG | TGC | TTC | AGA | GCC | AAC | TGC | GAG | TAC | CAG | TGC | CAG | CCC | CTG | 1332 |
| Val | Asp | Pro | Cys | Phe | Arg | Ala | Asn | Cys | Glu | Tyr | Gln | Cys | Gln | Pro | Leu |  |
|  |  | 350 |  |  |  |  | 355 |  |  |  |  | 360 |  |  |  |  |
| AAC | CAA | ACT | AGC | TAC | CTC | TGC | GTC | TGC | GCC | GAG | GGC | TTC | GCG | CCC | ATT | 1380 |
| Asn | Gln | Thr | Ser | Tyr | Leu | Cys | Val | Cys | Ala | Glu | Gly | Phe | Ala | Pro | Ile |  |
|  | 365 |  |  |  |  | 370 |  |  |  |  | 375 |  |  |  |  |  |
| CCC | CAC | GAG | CCG | CAC | AGG | TGC | CAG | ATG | TTT | TGC | AAC | CAG | ACT | GCC | TGT | 1428 |
| Pro | His | Glu | Pro | His | Arg | Cys | Gln | Met | Phe | Cys | Asn | Gln | Thr | Ala | Cys |  |
| 380 |  |  |  |  | 385 |  |  |  |  | 390 |  |  |  |  | 395 |  |
| CCA | GCC | GAC | TGC | GAC | CCC | AAC | ACC | CAG | GCT | AGC | TGT | GAG | TGC | CCT | GAA | 1476 |
| Pro | Ala | Asp | Cys | Asp | Pro | Asn | Thr | Gln | Ala | Ser | Cys | Glu | Cys | Pro | Glu |  |
|  |  |  |  | 400 |  |  |  |  | 405 |  |  |  |  | 410 |  |  |
| GGC | TAC | ATC | CTG | GAC | GAC | GGT | TTC | ATC | TGC | ACG | GAC | ATC | GAC | GAG | TGC | 1524 |
| Gly | Tyr | Ile | Leu | Asp | Asp | Gly | Phe | Ile | Cys | Thr | Asp | Ile | Asp | Glu | Cys |  |
|  |  |  | 415 |  |  |  |  | 420 |  |  |  |  | 425 |  |  |  |
| GAA | AAC | GGC | GGC | TTC | TGC | TCC | GGG | GTG | TGC | CAC | AAC | CTC | CCC | GGT | ACC | 1572 |
| Glu | Asn | Gly | Gly | Phe | Cys | Ser | Gly | Val | Cys | His | Asn | Leu | Pro | Gly | Thr |  |
|  |  | 430 |  |  |  |  | 435 |  |  |  |  | 440 |  |  |  |  |
| TTC | GAG | TGC | ATC | TGC | GGG | CCC | GAC | TCG | GCC | CTT | GTC | CGC | CAC | ATT | GGC | 1620 |
| Phe | Glu | Cys | Ile | Cys | Gly | Pro | Asp | Ser | Ala | Leu | Val | Arg | His | Ile | Gly |  |
|  | 445 |  |  |  |  | 450 |  |  |  |  | 455 |  |  |  |  |  |
| ACC | GAC | TGT | GAC | TCC | GGC | AAG | GTC | GAC | GAC | GAG | GCC | AGC | GGC | TCT | GGC | 1668 |
| Thr | Asp | Cys | Asp | Ser | Gly | Lys | Val | Asp | Asp | Glu | Ala | Ser | Gly | Ser | Gly |  |
| 460 |  |  |  |  | 465 |  |  |  |  | 470 |  |  |  |  | 475 |  |
| GAC | TGACTCGAG |  |  |  |  |  |  |  |  |  |  |  |  |  |  | 1680 |
| Asp |  |  |  |  |  |  |  |  |  |  |  |  |  |  |  |  |

( 2 ) INFORMATION FOR SEQ ID NO:16:

( i ) SEQUENCE CHARACTERISTICS:
        ( A ) LENGTH: 494 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

Met Leu Gly Val Leu Val Leu Gly Ala Leu Ala Leu Ala Gly Leu Gly

-continued

|     |     |     |     |     |     |     |     |     |     |     |     |     |
|-----|-----|-----|-----|-----|-----|-----|-----|-----|-----|-----|-----|-----|
| -18 |     | -15 |     |     |     | -10 |     |     |     | -5  |     |     |
| Phe | Pro | Ala | Pro | Ala | Glu | Pro | Gln | Pro | Gly | Gly | Ser | Gln | Cys | Val | Glu |
|     |     | 1   |     |     | 5   |     |     |     |     | 10  |     |     |
| His | Asp | Cys | Phe | Ala | Leu | Tyr | Pro | Gly | Pro | Ala | Thr | Phe | Leu | Asn | Ala |
| 15  |     |     |     |     | 20  |     |     |     |     | 25  |     |     |     |     | 30  |
| Ser | Gln | Ile | Cys | Asp | Gly | Leu | Arg | Gly | His | Leu | Met | Thr | Val | Arg | Ser |
|     |     |     |     | 35  |     |     |     |     | 40  |     |     |     |     | 45  |     |
| Ser | Val | Ala | Ala | Asp | Val | Ile | Ser | Leu | Leu | Leu | Asn | Gly | Asp | Gly | Gly |
|     |     |     | 50  |     |     |     |     | 55  |     |     |     |     | 60  |     |     |
| Val | Gly | Arg | Arg | Arg | Leu | Trp | Ile | Gly | Leu | Gln | Leu | Pro | Pro | Gly | Cys |
|     |     | 65  |     |     |     |     | 70  |     |     |     |     | 75  |     |     |     |
| Gly | Asp | Pro | Lys | Arg | Leu | Gly | Pro | Leu | Arg | Gly | Phe | Gln | Trp | Val | Thr |
|     | 80  |     |     |     |     | 85  |     |     |     |     | 90  |     |     |     |     |
| Gly | Asp | Asn | Asn | Thr | Ser | Tyr | Ser | Arg | Trp | Ala | Arg | Leu | Asp | Leu | Asn |
| 95  |     |     |     | 100 |     |     |     |     | 105 |     |     |     |     | 110 |     |
| Gly | Ala | Pro | Leu | Cys | Gly | Pro | Leu | Cys | Val | Ala | Val | Ser | Ala | Ala | Glu |
|     |     |     |     | 115 |     |     |     | 120 |     |     |     |     | 125 |     |     |
| Ala | Thr | Val | Pro | Ser | Glu | Pro | Ile | Trp | Glu | Glu | Gln | Cys | Glu | Val |
|     |     |     | 130 |     |     |     |     | 135 |     |     |     | 140 |     |     |
| Lys | Ala | Asp | Gly | Phe | Leu | Cys | Glu | Phe | His | Phe | Pro | Ala | Thr | Cys | Arg |
|     |     | 145 |     |     |     |     | 150 |     |     |     |     | 155 |     |     |     |
| Pro | Leu | Ala | Val | Glu | Pro | Gly | Ala | Ala | Ala | Ala | Val | Ser | Ile | Thr |
|     | 160 |     |     |     |     | 165 |     |     |     |     | 170 |     |     |     |
| Tyr | Gly | Thr | Pro | Phe | Ala | Ala | Arg | Gly | Ala | Asp | Phe | Gln | Ala | Leu | Pro |
| 175 |     |     |     |     | 180 |     |     |     |     | 185 |     |     |     |     | 190 |
| Val | Gly | Ser | Ser | Ala | Ala | Val | Ala | Pro | Leu | Gly | Leu | Gln | Leu | Met | Cys |
|     |     |     |     | 195 |     |     |     |     | 200 |     |     |     |     | 205 |     |
| Thr | Ala | Pro | Pro | Gly | Ala | Val | Gln | Gly | His | Trp | Ala | Arg | Glu | Ala | Pro |
|     |     |     | 210 |     |     |     |     | 215 |     |     |     |     | 220 |     |     |
| Gly | Ala | Trp | Asp | Cys | Ser | Val | Glu | Asn | Gly | Gly | Cys | Glu | His | Ala | Cys |
|     |     | 225 |     |     |     |     | 230 |     |     |     |     | 235 |     |     |     |
| Asn | Ala | Ile | Pro | Gly | Ala | Pro | Arg | Cys | Gln | Cys | Pro | Ala | Gly | Ala | Ala |
|     | 240 |     |     |     |     | 245 |     |     |     |     | 250 |     |     |     |     |
| Leu | Gln | Ala | Asp | Gly | Arg | Ser | Cys | Thr | Ala | Ser | Ala | Thr | Gln | Ser | Cys |
| 255 |     |     |     |     | 260 |     |     |     |     | 265 |     |     |     |     | 270 |
| Asn | Asp | Leu | Cys | Glu | His | Phe | Cys | Val | Pro | Asn | Pro | Asp | Gln | Pro | Gly |
|     |     |     |     | 275 |     |     |     |     | 280 |     |     |     |     | 285 |     |
| Ser | Tyr | Ser | Cys | Met | Cys | Glu | Thr | Gly | Tyr | Arg | Leu | Ala | Ala | Asp | Gln |
|     |     |     | 290 |     |     |     |     | 295 |     |     |     |     | 300 |     |     |
| His | Arg | Cys | Glu | Asp | Val | Asp | Asp | Cys | Ile | Leu | Glu | Pro | Ser | Pro | Cys |
|     |     | 305 |     |     |     |     | 310 |     |     |     |     | 315 |     |     |     |
| Pro | Gln | Arg | Cys | Val | Asn | Thr | Gln | Gly | Gly | Phe | Glu | Cys | His | Cys | Tyr |
|     | 320 |     |     |     |     | 325 |     |     |     |     | 330 |     |     |     |     |
| Pro | Asn | Tyr | Asp | Leu | Val | Asp | Gly | Glu | Cys | Val | Glu | Pro | Val | Asp | Pro |
| 335 |     |     |     |     | 340 |     |     |     |     | 345 |     |     |     |     | 350 |
| Cys | Phe | Arg | Ala | Asn | Cys | Glu | Tyr | Gln | Cys | Gln | Pro | Leu | Asn | Gln | Thr |
|     |     |     |     | 355 |     |     |     |     | 360 |     |     |     |     | 365 |     |
| Ser | Tyr | Leu | Cys | Val | Cys | Ala | Glu | Gly | Phe | Ala | Pro | Ile | Pro | His | Glu |
|     |     |     | 370 |     |     |     |     | 375 |     |     |     |     | 380 |     |     |
| Pro | His | Arg | Cys | Gln | Met | Phe | Cys | Asn | Gln | Thr | Ala | Cys | Pro | Ala | Asp |
|     |     | 385 |     |     |     |     | 390 |     |     |     |     | 395 |     |     |     |
| Cys | Asp | Pro | Asn | Thr | Gln | Ala | Ser | Cys | Glu | Cys | Pro | Glu | Gly | Tyr | Ile |
|     | 400 |     |     |     |     | 405 |     |     |     |     | 410 |     |     |     |     |
| Leu | Asp | Asp | Gly | Phe | Ile | Cys | Thr | Asp | Ile | Asp | Glu | Cys | Glu | Asn | Gly |
| 415 |     |     |     |     | 420 |     |     |     |     | 425 |     |     |     |     | 430 |

```
Gly Phe Cys Ser Gly Val Cys His Asn Leu Pro Gly Thr Phe Glu Cys
                435                 440                 445

Ile Cys Gly Pro Asp Ser Ala Leu Val Arg His Ile Gly Thr Asp Cys
            450                 455                 460

Asp Ser Gly Lys Val Asp Asp Glu Ala Ser Gly Ser Gly Asp
            465                 470                 475
```

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="acidic amino acid"

( i x ) FEATURE:
        ( A ) NAME/KEY: Modified-site
        ( B ) LOCATION: 2
        ( D ) OTHER INFORMATION: /note="acidic amino acid"

( x i ) SEQUENCE DESCRIPTION: SEQ ID NO:17:

```
Xaa Xaa Xaa Ser Gly Ser Gly Xaa
1               5
```

( 2 ) INFORMATION FOR SEQ ID NO:18:

( i ) SEQUENCE CHARACTERISTICS:
        ( A ) LENGTH: 476 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 469
        ( D ) OTHER INFORMATION: /note="acidic amino acid"

( i x ) FEATURE:
        ( A ) NAME/KEY: Modified-site
        ( B ) LOCATION: 470
        ( D ) OTHER INFORMATION: /note="acidic amino acid"

( x i ) SEQUENCE DESCRIPTION: SEQ ID NO:18:

```
Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
                20                  25                  30

Ile Cys Asp Gly Leu Arg Gly His Leu Met Thr Val Arg Ser Ser Val
            35                  40                  45

Ala Ala Asp Val Ile Ser Leu Leu Asn Gly Asp Gly Val Gly
        50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
            115                 120                 125

Val Pro Ser Glu Pro Ile Trp Glu Glu Gln Gln Cys Glu Val Lys Ala
```

|   |   |   |   |   | 130 |   |   |   |   | 135 |   |   |   |   | 140 |   |   |   |
|---|---|---|---|---|---|---|---|---|---|---|---|---|---|---|---|---|---|---|
| Asp 145 | Gly | Phe | Leu | Cys | Glu 150 | Phe | His | Phe | Pro | Ala 155 | Thr | Cys | Arg | Pro | Leu 160 | | | |
| Ala | Val | Glu | Pro | Gly 165 | Ala | Ala | Ala | Ala | Ala 170 | Val | Ser | Ile | Thr | Tyr 175 | Gly | | | |
| Thr | Pro | Phe | Ala 180 | Ala | Arg | Gly | Ala | Asp 185 | Phe | Gln | Ala | Leu | Pro 190 | Val | Gly | | | |
| Ser | Ser | Ala 195 | Ala | Val | Ala | Pro | Leu 200 | Gly | Leu | Gln | Leu | Met 205 | Cys | Thr | Ala | | | |
| Pro | Pro 210 | Gly | Ala | Val | Gln | Gly 215 | His | Trp | Ala | Arg | Glu 220 | Ala | Pro | Gly | Ala | | | |
| Trp 225 | Asp | Cys | Ser | Val | Glu 230 | Asn | Gly | Gly | Cys | Glu 235 | His | Ala | Cys | Asn | Ala 240 | | | |
| Ile | Pro | Gly | Ala | Pro 245 | Arg | Cys | Gln | Cys | Pro 250 | Ala | Gly | Ala | Ala | Leu 255 | Gln | | | |
| Ala | Asp | Gly | Arg 260 | Ser | Cys | Thr | Ala | Ser 265 | Ala | Thr | Gln | Ser | Cys 270 | Asn | Asp | | | |
| Leu | Cys | Glu 275 | His | Phe | Cys | Val | Pro 280 | Asn | Pro | Asp | Gln | Pro 285 | Gly | Ser | Tyr | | | |
| Ser | Cys 290 | Met | Cys | Glu | Thr | Gly 295 | Tyr | Arg | Leu | Ala | Ala 300 | Asp | Gln | His | Arg | | | |
| Cys 305 | Glu | Asp | Val | Asp | Asp 310 | Cys | Ile | Leu | Glu | Pro 315 | Ser | Pro | Cys | Pro | Gln 320 | | | |
| Arg | Cys | Val | Asn | Thr 325 | Gln | Gly | Gly | Phe | Glu 330 | Cys | His | Cys | Tyr | Pro 335 | Asn | | | |
| Tyr | Asp | Leu | Val 340 | Asp | Gly | Glu | Cys | Val 345 | Glu | Pro | Val | Asp | Pro 350 | Cys | Phe | | | |
| Arg | Ala | Asn 355 | Cys | Glu | Tyr | Gln | Cys 360 | Gln | Pro | Leu | Asn | Gln 365 | Thr | Ser | Tyr | | | |
| Leu | Cys 370 | Val | Cys | Ala | Glu | Gly 375 | Phe | Ala | Pro | Ile | Pro 380 | His | Glu | Pro | His | | | |
| Arg 385 | Cys | Gln | Met | Phe | Cys 390 | Asn | Gln | Thr | Ala | Cys 395 | Pro | Ala | Asp | Cys | Asp 400 | | | |
| Pro | Asn | Thr | Gln | Ala 405 | Ser | Cys | Glu | Cys | Pro 410 | Glu | Gly | Tyr | Ile | Leu 415 | Asp | | | |
| Asp | Gly | Phe | Ile 420 | Cys | Thr | Asp | Ile | Asp 425 | Glu | Cys | Glu | Asn | Gly 430 | Gly | Phe | | | |
| Cys | Ser | Gly 435 | Val | Cys | His | Asn | Leu 440 | Pro | Gly | Thr | Phe | Glu 445 | Cys | Ile | Cys | | | |
| Gly | Pro 450 | Asp | Ser | Ala | Leu | Val 455 | Arg | His | Ile | Gly | Thr 460 | Asp | Cys | Asp | Ser | | | |
| Gly 465 | Lys | Val | Asp | Xaa 470 | Xaa | Xaa | Ser | Gly | Ser 475 | Gly | Xaa | | | | | | | |